(12) United States Patent
Portnoy et al.

(10) Patent No.: US 10,801,030 B2
(45) Date of Patent: Oct. 13, 2020

(54) GENERAL SECRETORY PATHWAY (GSP) MUTANT LISTERIA SPP., AND METHODS FOR MAKING AND USING THE SAME

(71) Applicant: The Regents of the University of California, Oakland, CA (US)

(72) Inventors: Daniel A. Portnoy, Albany, CA (US); Juliana Durack, San Francisco, CA (US); Thomas P. Burke, Berkeley, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 422 days.

(21) Appl. No.: 15/521,586

(22) PCT Filed: Nov. 4, 2015

(86) PCT No.: PCT/US2015/590070
§ 371 (c)(1),
(2) Date: Apr. 24, 2017

(87) PCT Pub. No.: WO2016/073585
PCT Pub. Date: May 12, 2016

(65) Prior Publication Data
US 2017/0342423 A1    Nov. 30, 2017

Related U.S. Application Data

(60) Provisional application No. 62/075,756, filed on Nov. 5, 2014.

(51) Int. Cl.
*C12N 15/74* (2006.01)
*C07K 14/195* (2006.01)
*A61K 39/02* (2006.01)
*C12N 1/20* (2006.01)
*A61K 48/00* (2006.01)

(52) U.S. Cl.
CPC .............. *C12N 15/74* (2013.01); *A61K 39/02* (2013.01); *C07K 14/195* (2013.01); *C12N 1/20* (2013.01); *A61K 48/00* (2013.01)

(58) Field of Classification Search
None
See application file for complete search history.

(56) References Cited

U.S. PATENT DOCUMENTS

2011/0287055 A1    11/2011    Lauer et al.
2012/0121643 A1*   5/2012    Dubensky, Jr. ....  A61K 39/0011
                                                    424/200.1

FOREIGN PATENT DOCUMENTS

WO    WO 03/092600 A2    11/2003
WO    WO 03/102168 A1    12/2003
WO    WO 2008/066774 A2    6/2008

OTHER PUBLICATIONS

Schmidt et al. J. Biol. Chem., 275:15440-48 (Year: 2000).*
Bondar et al. "Dynamics of SecY Translocons with Translocation-Defective Mutations," Structure, vol. 18, No. 7, 2010, pp. 847-857.
Chandrabos et al. "The p60 and NamA Autolysins from *Listeria monocytogenes* Contribute to Host Colonization and Induction of Protective Memory," Cell Microbiology, vol. 17, No. 2, Feb. 2015, pp. 147-163.
Desvaux et al. "The protein secretion systems in Listeria: inside out bacterial virulence," FEMS Microbial Review, vol. 30, No. 5, 2006, pp. 774-805.
Durack et al. "A prl Mutation in SecY Suppresses Secretion and Virulence Defects of Listeria monocytogenes secA2 Mutants," Journal of Bacteriology, vol. 197, No. 5, Mar. 2015 (Published Online Dec. 22, 2014), pp. 932-942.
Flower, Ann M. "The SecY translocation complex: convergence of genetics and structure," Trends in Microbiology, vol. 15, No. 5, May 2007, pp. 203-210.
Halbedel et al. "A Systematic Proteomic Analysis of *Listeria monocytogenes* House-keeping Protein Secretion Systems," Molecular & Cellular Proteomics, vol. 13, No. 11, Nov. 2014 (Published Online Jul. 23, 2014), pp. 3063-3081.
Lycklama et al. "Immobilization of the plug domain inside the SecY channel allows unrestricted protein translocation," The Journal of Biological Chemistry, vol. 285, No. 31, Jul. 30, 2010, pp. 23747-23754.
NCBI Genbank, NCBI_NC_00321_SecA_SecY, *Listeria monocytogenes* strain EGO, complete genome, Nov. 8, 2011 [online]. [Retrieved on May 1, 2016]. Retrieved from the Internet: <URL: http://www.ncbi.nlm.nih.gov/nuccore/16802048?sat=8&satkey=2081954>, 3 pages.
Osborne, "PrlA suppressor mutations cluster in regions corresponding to three distinct topological domains," The EMBO Journal, vol. 12, No. 9, 1993, pp. 3391-3398.
Smith et al. "Modeling the effects of prl mutations on the *Escherichia coli* SecY complex," Journal of Bacteriology, vol. 187, No. 18, Sep. 2005, pp. 6454-6465.
Van Der Wolk et al. "PrlA4 prevents the rejection of signal sequence defective preproteins by stabilizing the SecA-SecY interaction during the initiation of translocation," The EMBO Journal, vol. 17, No. 13, 1998, pp. 3631-3639.

* cited by examiner

*Primary Examiner* — Nancy A Treptow
(74) *Attorney, Agent, or Firm* — Bret E. Field; Bozicevic, Field & Francis LLP

(57) ABSTRACT

General secretory pathway (GSP) mutant *Listeria* bacteria are provided. Aspects of the bacteria include the presence of a GSP mutation, e.g., a SecY and/or SecA mutation. Also provided are methods of making and using the *Listeria* bacteria comprising a GSP mutation as vectors and vaccines expressing a heterologous nucleic acid.

11 Claims, 8 Drawing Sheets
Specification includes a Sequence Listing.

GENERAL SECRETORY PATHWAY (GSP) MUTANT LISTERIA SPP., AND METHODS FOR MAKING AND USING THE SAME

CROSS-REFERENCE TO RELATED APPLICATIONS

Pursuant to 35 U.S.C. § 119(e), this application claims priority to the filing date of U.S. Provisional Patent Application No. 62/075,756, filed Nov. 5, 2014; the disclosure of which application is herein incorporated by reference.

GOVERNMENT RIGHTS

This invention was made with Government support under contracts AI027655 and AI063302 awarded by the National Institutes of Health. The Government has certain rights in the invention.

INTRODUCTION

The use of vaccines is a cost-effective medical tool for the management of infectious diseases, including infectious diseases caused by bacteria, viruses, parasites, and fungi. In addition to effecting protection against infectious diseases, effort is also being expended to develop vaccines that stimulate the host's immune system to intervene in tumor growth.

Host immune responses include both the humoral immune response involving antibody production and the cell-mediated immune response. Protective immunization via vaccine has usually been designed to induce the formation of humoral antibodies directed against infectious agents, tumor cells, or the action of toxins. However, the control of certain diseases characterized by the presence of tumor cells or by chronic infection of cells with infectious agents, often requires a cell-mediated immune response either in place of, or in addition to the generation of antibody. While the humoral immune response may be induced using live infectious agents and agents that have been inactivated, a cellular immune response is most effectively induced through the use of live agents as vaccines. Such live agents include live infectious agents which may gain access to the cytoplasm of host cells where the proteins encoded by these agents are processed into epitopes which when presented to the cellular immune system, induce a protective response.

Microorganisms, particularly *Salmonella* and *Shigella*, which have been attenuated using a variety of mechanisms have been examined for their ability to encode and express heterologous antigens. Such bacteria may be useful as live attenuated bacterial vaccines which serve to induce a cellular immune response directed against a desired heterologous antigen.

*Listeria monocytogenes* is a Gram-positive, food-borne human and animal pathogen responsible for serious infections in immunocompromised individuals and pregnant women. Severe *L. monocytogenes* infections in humans are characterized by meningitis, meningoencephalitis, septicemia, and fetal death. *L. monocytogenes* is ubiquitous in nature and, in addition, can be isolated from a wide variety of warm-blooded animals.

*L. monocytogenes* elicits a predominantly cellular immune response when inoculated into an animal. As such, *L. monocytogenes* has been used widely as an experimental model to study many aspects of infection and immunity. Importantly, infection of mice with sublethal doses of *L. monocytogenes* results in the induction of long-lived cell-mediated immunity (CMI). In preclinical studies, attenuated strains of *L. monocytogenes* have shown tremendous potential as recombinant vaccine vectors. More importantly, attenuated recombinant strains have shown clinical efficacy as therapeutic vaccines for cancer immunotherapy. In principle, may different antigens can be expressed and secreted, but in practice, many antigens have proven difficult to express or secrete or expression/secretion has had detrimental impact on the vaccine strain.

SUMMARY

General secretory pathway (GSP) mutant *Listeria* bacteria are provided. Aspects of the bacteria include the presence of a general secretory pathway (GSP) mutation, e.g., a SecY and/or SecA mutant. Also provided are methods of making and using the bacteria, e.g., as vectors and vaccines.

BRIEF DESCRIPTION OF THE FIGURES

FIG. 3A) Fluorescent microscopy of ΔsecA2 and R57. Mid-exponential phase cells were stained with SYTO9 green. FIG. 3B). Disk diffusion susceptibility to 1 mg of lysozyme expressed as ratio of WT, where a ratio>1 indicates increased susceptibility to lysozyme. Error bars represent standard deviations of the mean zone ratio. A Student's t-test was used to analyze statistical significance where *, P<0.0001 and ns—P≥0.05. Bacterial burdens in FIG. 3C) spleens and FIG. 3D) livers 48 hr post infection with $1 \times 10^5$ CFU in CD1 mice. The dashed-line represents the limit of detection. Results show CFU from three independent experiments. Statistical significance was evaluated using a Mann Whitney test. *P<0.0001, ns—P≥0.05.

FIG. 4A) Swarming motility of mutants and strains complemented with the lmo2767 operon was assessed on semi-solid LB agar following incubation at 30° C. after 48 hr. Motility is expressed as a percentage of the swarming area of the WT strain and set at 100% (represented by a red dotted line). Error bars represent standard deviations of the mean zone ratio between three independent experiments. FIG. 4B) Disk diffusion susceptibility to 1 mg of lysozyme expressed as a ratio of WT. Error bars represent standard deviations of the mean zone ratio. FIG. 4C) and FIG. 4D) Plaque area of each mutant is shown as a percentage when compared to the WT strain set at 100% (represented by a red dotted line). Error bars represent standard deviations of the mean plaque size ratio between three independent experiments. A Student's t-test was used to analyze statistical significance where ***, P<0.0001; *, P<0.05 and ns—P≥0.05.

FIG. 5A) Swarming motility of mutants and strains complemented with lmo2767 operon was assessed on semi-solid LB agar following incubation at 30° C. after 48 hr. Motility is expressed as a percentage of swarming area of the WT strain and set at 100% (represented by a red dotted line). Error bars represent standard deviations of the mean zone ratio between three independent experiments. FIG. 5B) Plaque area of each mutant is shown as a percentage when compared to the WT strain set at 100% (represented by a red dotted line). Error bars represent standard deviations of the mean plaque size ratio between three independent experiments. A Student's t-test was used to analyze statistical significance where ***, P<0.0001; *, P<0.05 and ns—P≥0.05. FIGS. 5C & 5D) Secreted levels of P60 in supernatants from mid-log cultured cells, quantified by western blotting with inserted images of gels. Bacterial burdens in FIG. 5E) spleens and FIG. 5F) livers 48 hr post IV infection of $1 \times 10^5$ CFU in mice, showing data from three independent experiments. The dashed-line represents the limit of detection. Statistical significance was evaluated using a Mann Whitney test. ***P<0.0001, *P<0.05, ns—P≥0.05.

FIGS. 6A and 6D) Disk diffusion susceptibility to 10 μg of vancomycin, FIGS. 6B and 6E) 120 μg of penicillin and FIGS. 6C and 6F) 1 mg of lysozyme expressed as ratio of WT, where a ratio>1 indicates increased susceptibility. Error bars represent standard deviations of the mean zone ratio of WT. Student's t-test was used to analyze statistical significance where ***, P<0.0001 and ns—P≥0.05.

FIG. 8C) Plaque area of each mutant is shown as a percentage when compared to the WT strain. Error bars represent standard deviations from the mean between three independent experiments. Student's t-test was used to analyze statistical significance where ***, P<0.0001; *, P<0.05 and ns—P≥0.05. FIG. 8D) An image of a western blot showing P60 in supernatants from mid-log (5 h) cultured cells in LB broth. FIG. 8E) Secreted levels of P60 in supernatants from mid-log (5 h) cultured cells in LB broth expressed as a percentage of protein secreted by the WT strain.

DETAILED DESCRIPTION

Figure 1:
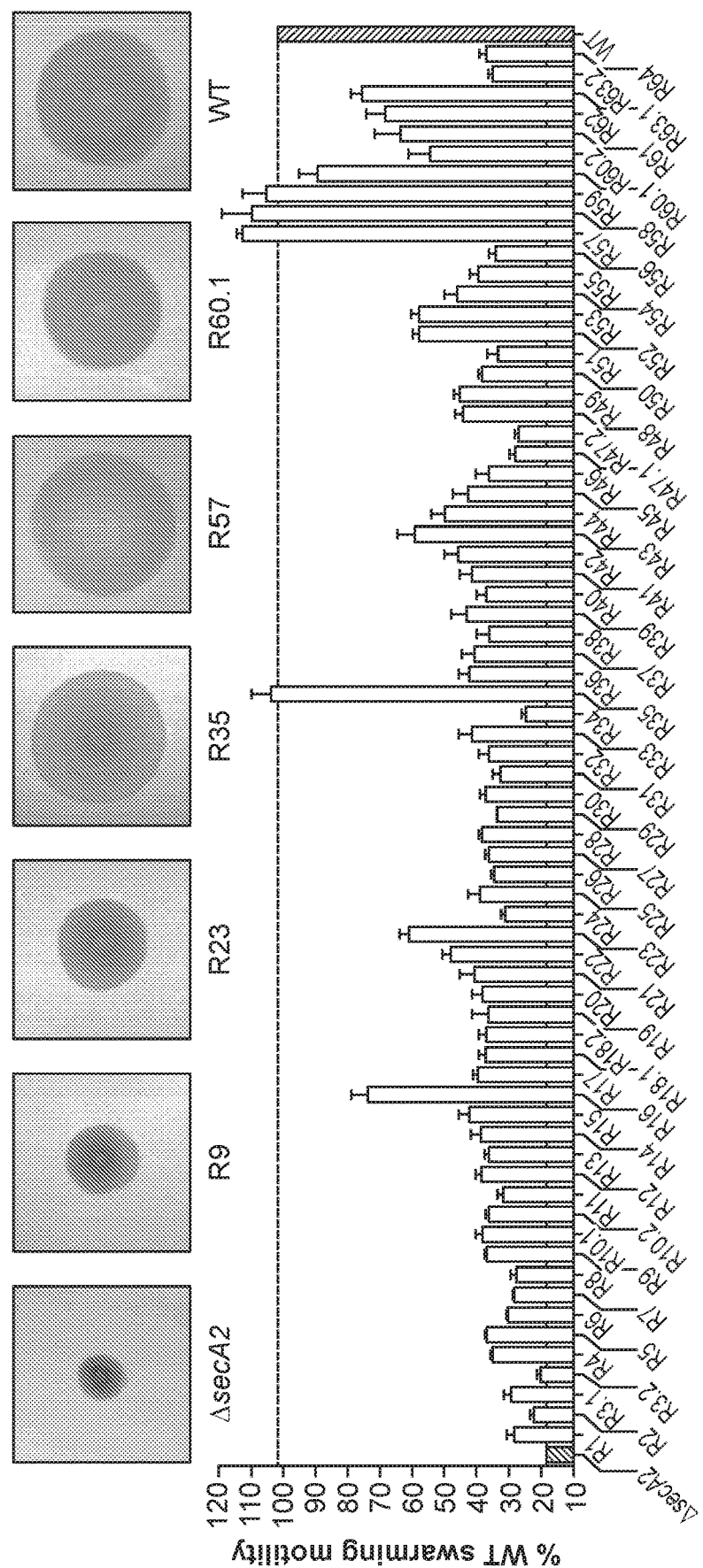
FIG. 1: Swarming motility of suppressor mutants. Motility assessed on semi-solid LB agar following incubation at 30° C. after 48 hr. Motility is expressed as a percentage of swarming area of the WT strain seeded on the same plate. Error bars represent standard deviations of the mean zone ratio between three independent experiments. Images show motility zones for the suppressor mutants indicated.

General secretory pathway (GSP) mutant *Listeria* bacteria are provided. Aspects of the bacteria include the presence of a general secretory pathway (GSP) mutation, e.g., a SecY and/or SecA mutant. Also provided are methods of making and using the bacteria, e.g., as vectors and vaccines.

Before the present invention is described in greater detail, it is to be understood that aspects of the present disclosure are not limited to the particular embodiments described, and as such may, of course, vary. It is also to be understood that the terminology used herein is for the purpose of describing particular embodiments only, and is not intended to be limiting, since the scope of embodiments of the present disclosure will be defined only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within embodiments of the present disclosure. The upper and lower limits of these smaller ranges may independently be included in the smaller ranges and are also encompassed within embodiments of the present disclosure, subject to any specifically excluded limit in the stated range. Where the stated range includes one or both of the limits, ranges excluding either or both of those included limits are also included in embodiments of the present disclosure.

Unless defined otherwise, all technical and scientific terms used herein have the same meaning as commonly understood by one of ordinary skill in the art to which this invention belongs. Although any methods and materials similar or equivalent to those described herein can also be used in the practice or testing of embodiments of the present disclosure, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that embodiments of the present disclosure are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing the subject invention, the subject bacteria are reviewed first in greater detail, followed by a review of representative applications in which the subject bacteria and methods find use.

General Secretory Pathway (GSP) Mutant *Listeria* Bacteria

As summarized above, aspects of the invention include general secretory pathway (GSP) mutant *Listeria* bacteria. The subject bacteria may be any *Listeria* species that includes a GSP mutation, e.g., as described below. *Listeria* spp of interest include, but are not limited to: *L. fleischmannii, L. grayi, L. innocua, L. ivanovii, L. marthii, L. monocytogenes, L. rocourtiae, L. seeligeri, L. weihenstephanen-*

*sis,* and *L. welshimeri.* Thus, strains of *Listeria* other than *L. monocytogenes* may be used for the generation of bacteria according to the present invention. In certain embodiments, the *Listeria* strain is *L. monocytogenes.*

As the *Listeria* bacteria include a GSP mutation, they are general secretory pathway (GSP) mutants. As such, the bacteria include a mutant member(s) of the general secretory pathway (GSP) (i.e., Secretion system or Sec). Members of the GSP include various GSP pathway proteins, including: transmembrane components, e.g., SecY, SecE, SecG, SecDF, YajC, YidC; Cytoplasmic components, e.g., FtsY and Ffh; ATPases, e.g., SecA, SecA2; Signal peptidases I; e.g., SipX, SipY, SipZ; and Signal peptidases II, e.g., Lsp and LspB. Bacteria according to embodiments of the invention may include one or more mutant GSP proteins, such as two or more, three or more, including four or more GSP mutant proteins, where in some instances the number of mutant GSP proteins is five or less, such as four or less.

In some instances, the GSP mutation confers enhanced protein secretion onto the bacteria (as compared to a suitable control). The enhancement may be manifested in one or more ways. For example, the GSP mutation may increase the amount of a given protein that is secreted by the bacteria, where the magnitude of increase may vary, and in some instances may be 2-fold or greater, such as 5-fold or greater. For example, in some instances the GSP mutation, such as a SecY mutation, provides for an increase in the secretion of p60, where the magnitude of increase may vary, and in some instances may be 2-fold or greater, such as 5-fold or greater. In some instances, the GSP mutation may increase the diversity of proteins that are secreted by the bacteria, where the magnitude of increase may vary, and in some instances may be 2-fold or greater, such as 5-fold or greater. In some instances, the GSP mutation may decrease the toxicity associated with expression/secretion of a given protein that is secreted by the bacteria, where the magnitude of decrease may vary, and in some instances may be 2-fold or greater, such as 5-fold or greater.

As indicated above, the GSP mutation may include one or more mutant GSP proteins. In some instances, the mutant GSP protein is a transmembrane component, e.g., SecY, SecE, SecG, SecDF, YajC, YidC. In some embodiments, the mutant GSP protein is SecY. Of interest are SecY mutants that result in a conformational change of a translocation pore configuration, e.g., a change in the Sec translocon configuration, which translocon is made up of SecY, SecE and SecG. Conformational changes of interest include changes that result in enhanced protein secretion, e.g., as described above. In some instances, the SecY mutant includes a protein localization (Prl) mutation. Prl mutations are mutations that may be characterized as gain-of-function mutations that expand the repertoire of substrates that can be exported. Prl mutations of interest include PrlA1, and the like.

The SecY mutant may include a variety of different types of mutations in a variety of different locations of the protein. Mutations of interest include insertion, deletion and substitution mutations. In some instances, the mutation is located in a transmembrane helix domain of the SecY protein, such as the tenth transmembrane helix. In some instances, the mutation is a substitution mutation, e.g., a substitution of a single amino acid residue. Of interest are non-conserved substitutions, e.g., a substitution of a hydrophobic (e.g., A, G, I, F, C, L, M, V) for a hydrophilic (e.g., R, E, K, D, H, N, Q, S, T) residue. In some instances, the SecY mutant includes a mutation at G408, such as G408R (where amino acid number is based on wild type *L. monocytogenes* SecY and analogous positions may be readily decided in other *Listeria* SecY proteins).

In some instances, the mutant GSP protein is an ATPase, e.g., SecA, SecA2. SecA mutants of interest include proteins having an AZI mutation (i.e., an azide resistance mutation). The SecA mutant may include a variety of different types of mutations in a variety of different locations of the protein. Mutations of interest include insertion, deletion and substitution mutations. In some instances, the mutation is a substitution mutation, e.g., a substitution of a single amino acid residue. Of interest are conserved substitutions, e.g., a substitution of one hydrophilic residue (e.g., R, E, K, D, H, N, Q, S, T) for another hydrophilic residue. In some instances, the SecA mutant includes a mutation at D599, such as D599N (where amino acid number is based on wild type *L. monocytogenes* SecA and analogous positions may be readily decided in other *Listeria* SecA proteins).

A given bacteria is considered to have a GSP mutation, e.g., as described above, if it includes a mutant GSP protein and/or a mutant nucleic acid coding sequence therefor. For example, SecY mutant bacteria may include a mutation in lmo2612, where the mutation may be an insertion, deletion or substitution, and in some instances is an SNP (e.g., as found in a prlA1 mutation) that encodes a mutant SecY, e.g., as described above. The mutant nucleic acid coding sequence of such embodiments may be integrated and/or episomally maintained, as desired.

In some instances, the bacteria are SecA2 mutant bacteria, by which is meant that they include a mutant SecA2 protein, which mutant protein is present in addition to the GSP protein mutation, e.g., SecY or SecA mutations, such as described above. The SecA2 mutant protein of such instances is a loss of function mutant. The SecA2 mutant may include a variety of different types of mutations in a variety of different locations of the protein. Mutations of interest include insertion, deletion and substitution mutations. Examples of SecA2 mutants of interest are described in the Experimental section, below.

In some embodiments, the *Listeria* bacteria are attenuated. The term "attenuated," as used herein, describes the diminution in the ability of the subject bacteria to cause disease in an animal as a whole, e.g., as measured by the $LD_{50}$ of the bacteria, as described below. More specifically, the pathogenic characteristics of the attenuated *Listeria* strain, as viewed from the vantage of the host animal as a whole (as opposed to a cell based perspective) have been lessened compared with wild-type *Listeria,* although the attenuated *Listeria* is capable of growth and maintenance in culture. In certain embodiments, bacteria are considered to be attenuated if, upon the intravenous inoculation of Balb/c mice (as described in the experimental section, below), the lethal dose at which 50% of inoculated animals survive ($LD_{50}$) is increased above the $LD_{50}$ of wild-type *Listeria* by at least about 10-fold, such as by at least about 100-fold, including by at least about 1,000 fold, where in certain embodiments the magnitude of increase is at least about 10,000 fold, such as at least about 100,000-fold, as determined using the assay employed in the experimental section below. An attenuated strain of *Listeria* according to the subject invention is thus one which does not kill an animal to which it is administered, or is one which kills the animal only when the number of bacteria administered is vastly greater than the number of wild type non-attenuated bacteria which would be required to kill the same animal.

In certain embodiments, attenuated species according to the subject invention are ones that exhibit a decreased virulence compared to their corresponding wild type strain in the Competitive Index Assay as described in Auerbach et al., "Development of a Competitive Index Assay To Evaluate the Virulence of *Listeria monocytogenes* actA Mutants during Primary and Secondary Infection of Mice," Infection and Immunity, September 2001, p. 5953-5957, Vol. 69, No. 9. In this assay, mice are inoculated with test and reference, e.g., wild-type, strains of bacteria. Following a period of time, e.g., 48 to 60 hours, the inoculated mice are sacrificed and one or more organs, e.g., liver, spleen, are evaluated for bacterial abundance. In these embodiments, a given bacterial strain is considered to be less virulent if its abundance in the spleen is at least about 50-fold, or more, such as 70-fold or more less than that observed with the corresponding wild-type strain, and/or its abundance in the liver is at least about 10-fold less, or more, such as 20-fold or more less than that observed with the corresponding wild-type strain.

In yet other embodiments, bacteria are considered to be less virulent if they show abortive replication in less than about 8 hours, such as less than about 6 hours, including less than about 4 hours, as determined using the assay described in Jones and Portnoy, Intracellular growth of bacteria. (1994b) *Methods Enzymol.* 236:463-467. In yet other embodiments, bacteria are considered to be attenuated or less virulent if, compared to wild-type, they form smaller plaques in the plaque assay employed in U.S. Pat. No. 7,794,728 (the disclosure of which is herein incorporated by reference) where cells, such as murine L2 cells, are grown to confluency, e.g., in six-well tissue culture dishes, and then infected with bacteria. Subsequently, DME-agar containing gentamicin is added and plaques are grown for a period of time, e.g., 3 days. Living cells are then visualized by adding an additional DME-agar overlay, e.g., containing neutral red (GIBCO BRL) and incubated overnight. In such an assay, the magnitude in reduction in plaque size observed with the attenuated mutant as compared to the wild-type is, in certain embodiments, 10%, including 15%, such as 25% or more.

Attenuated bacteria of the invention may include one or more different mutations which confer the attenuated phenotype, where mutations of interest include hly mutations and/or IplA mutations, e.g., as described in U.S. Pat. No. 7,794,728 (the disclosure of which is herein incorporated by reference); actA and/or internalin B (InlB) mutations, e.g., as reported in Dung et al., Clin. Cancer Res. (2012) 18:858-868); etc.

A given *Listeria* host cell may include one or more modifications as compared to wildtype, which modifications provide for desirable qualities in the host cell, e.g., attenuation, enhanced immunogenicity, etc. Specific *Listeria* host cells that be assessed in embodiments of the invention include, but are not limited to, those described in PCT Published Application Nos.: WO 2014/106123; WO 2014/074635; WO 2009/143085; WO 2008027560 WO 2008066774; WO 2007117371; WO 2007103225; WO 2005071088; WO 2003102168; WO 2003/092600; WO/2000/009733; and WO 1999/025376; the disclosures of which applications are herein incorporated by reference.

In certain embodiments, bacteria according to the subject invention express a heterologous antigen. The heterologous antigen is, in certain embodiments, one that is capable of providing protection in an animal against challenge by the infectious agent from which the heterologous antigen was derived, or which is capable of affecting tumor growth and metastasis in a manner which is of benefit to a host organism. Heterologous antigens which may be introduced into a *Listeria* strain of the subject invention by way of DNA encoding the same thus include any antigen which when expressed by *Listeria* serves to elicit a cellular immune response which is of benefit to the host in which the response is induced. Heterologous antigens therefore include those specified by infectious agents, wherein an immune response directed against the antigen serves to prevent or treat disease caused by the agent. Such heterologous antigens include, but are not limited to, viral, bacterial, fungal or parasite surface proteins and any other proteins, glycoproteins, lipoprotein, glycolipids, and the like. Heterologous antigens also include those which provide benefit to a host organism which is at risk for acquiring or which is diagnosed as having a tumor that expresses the heterologous antigen(s). The host organism is may be a mammal, such as a human.

By the term "heterologous antigen," as used herein, is meant a protein or peptide, a glycoprotein or glycopeptide, a lipoprotein or lipopeptide, or any other macromolecule which is not normally expressed in *Listeria,* which substantially corresponds to the same antigen in an infectious agent, a tumor cell or a tumor-related protein. The heterologous antigen is expressed by a strain of *Listeria* according to the subject invention, and is processed and presented to cytotoxic T-cells upon infection of mammalian cells by the strain. The heterologous antigen expressed by *Listeria* species need not precisely match the corresponding unmodified antigen or protein in the tumor cell or infectious agent so long as it results in a T-cell response that recognizes the unmodified antigen or protein which is naturally expressed in the mammal. In other examples, the tumor cell antigen may be a mutant form of that which is naturally expressed in the mammal, and the antigen expressed by the *Listeria* species will conform to that tumor cell mutated antigen. By the term "tumor-related antigen," as used herein, is meant an antigen which affects tumor growth or metastasis in a host organism. The tumor-related antigen may be an antigen expressed by a tumor cell, or it may be an antigen which is expressed by a non-tumor cell, but which when so expressed, promotes the growth or metastasis of tumor cells. The types of tumor antigens and tumor-related antigens which may be introduced into *Listeria* by way of incorporating DNA encoding the same, include any known or heretofore unknown tumor antigen. In other examples, the "tumor-related antigen" has no effect on tumor growth or metastasis, but is used as a component of the *Listeria* vaccine because it is expressed specifically in the tissue (and tumor) from which the tumor is derived. In still other examples, the "tumor-related antigen" has no effect on tumor growth or metastasis, but is used as a component of the *Listeria* vaccine because it is selectively expressed in the tumor cell and not in any other normal tissues.

The heterologous antigen useful in vaccine development may be selected using knowledge available to the skilled artisan, and many antigenic proteins which are expressed by tumor cells or which affect tumor growth or metastasis or which are expressed by infectious agents are currently known. For example, viral antigens which may be considered as useful as heterologous antigens include but are not limited to the nucleoprotein (NP) of influenza virus and the gag protein of HIV. Other heterologous antigens include, but are not limited to, HIV env protein or its component parts gp120 and gp41, HIV nef protein, and the HIV pol proteins, reverse transcriptase and protease. Still other heterologous antigens can be those related to hepatitis C virus (HCV), including but not limited to the E1 and E2 glycoproteins, as well as non-structural (NS) proteins, for example NS3. In addition, other viral antigens such as herpesvirus proteins may be useful. The heterologous antigens need not be limited to being of viral origin. Parasitic antigens, such as, for example, malarial antigens, are included, as are fungal antigens, bacterial antigens and tumor antigens.

As noted herein, a number of proteins expressed by tumor cells are also known and are of interest as heterologous antigens which may be inserted into the vaccine strain of the invention. These include, but are not limited to, the bcr/abl antigen in leukemia, HPVE6 and E7 antigens of the oncogenic virus associated with cervical cancer, the MAGE1 and MZ2-E antigens in or associated with melanoma, and the MVC-1 and HER-2 antigens in or associated with breast cancer. Other coding sequences of interest include, but are not limited to: costimulatory molecules, immunoregulatory molecules, and the like.

In some instances, the heterologous antigen is one that is, or has been modified to be, secreted by a SecA2 mediated pathway. In some instances, the antigen is a protein having a domain that is recognized by SecA2 and secreted by a pathway in which SecA2 is involved. SecA2 recognized domains that may be present in the heterologous antigen include, but are not limited to those described in Renier et al., J. Proteomics (2013) 80:183-195. Such domains also include those found in: PBP 2B; N-acetylmuramidase (NamA); Pheromone transporter (OppA); p60 autolysin; Maltose/maltodextrin ABC transporter; Antigenic lipoprotein (Csa); Conserved lipoprotein; RNA polymerase β' subunit; RNA polymerase β subunit; Pyruvate dehydrogenase E2 subunit; Dnak; GroEL; EF-Tu; Enolase; Phosphomannose isomerase; Ribosomal protein L19; and Ribosomal protein S9. (See e.g., Lenz et al., Proc. Nat'l Acad. Sci. USA (2003) 100: 12432-12437).

Bacteria as described herein may be fabricated using a variety of different protocols. As such, generation of the subject attenuated bacteria may be accomplished in a number of ways that are well known to those of skill in the art, including deletion mutagenesis, insertion mutagenesis, and mutagenesis which results in the generation of frameshift mutations, mutations which effect premature termination of a protein, or mutation of regulatory sequences which affect gene expression. Mutagenesis can be accomplished using recombinant DNA techniques or using traditional mutagenesis technology using mutagenic chemicals or radiation and subsequent selection of mutants. Representative protocols of different ways to generate bacteria according to the present invention are provided in the Experimental Section, below.

The introduction of DNA encoding a heterologous antigen into a strain of *Listeria* may be accomplished, for example, by the creation of a recombinant *Listeria* in which DNA encoding the heterologous antigen is harbored on a vector, such as a plasmid for example, which plasmid is maintained and expressed in the *Listeria* species, and in whose antigen expression is under the control of prokaryotic promoter/regulatory sequences. Alternatively, DNA encoding the heterologous antigen may be stably integrated into the *Listeria* chromosome by employing, for example, transposon mutagenesis, homologous recombination, or integrase mediated site-specific integration (as described in application Ser. No. 10/136,860, the disclosure of which is herein incorporated by reference).

Several approaches may be employed to express the heterologous antigen in *Listeria* species as will be understood by one skilled in the art once armed with the present disclosure. In certain embodiments, genes encoding heterologous antigens are designed to either facilitate secretion of the heterologous antigen from the bacterium or to facilitate expression of the heterologous antigen on the *Listeria* cell surface.

In certain embodiments, a fusion protein which includes the desired heterologous antigen and a secreted or cell surface protein of *Listeria* is employed. Listerial proteins which are suitable components of such fusion proteins include, but are not limited to, listeriolysin O (LLO) and phosphatidylinositol-specific phospholipase (PI-PLC). A fusion protein may be generated by ligating the genes which encode each of the components of the desired fusion protein, such that both genes are in frame with each other. Thus, expression of the ligated genes results in a protein comprising both the heterologous antigen and the Listerial protein. Expression of the ligated genes may be placed under the transcriptional control of a Listerial promoter/regulatory sequence such that expression of the gene is effected during growth and replication of the organism. Signal sequences for cell surface expression and/or secretion of the fused protein may also be added to genes encoding heterologous antigens in order to effect cell surface expression and/or secretion of the fused protein. When the heterologous antigen is used alone (i.e., in the absence of fused *Listeria* sequences), it may be advantageous to fuse thereto signal sequences for cell surface expression and/or secretion of the heterologous antigen. The procedures for accomplishing this are well known in the art of bacteriology and molecular biology.

The DNA encoding the heterologous antigen which is expressed is, in some embodiments, preceded by a suitable promoter to facilitate such expression. The appropriate promoter/regulatory and signal sequences to be used will depend on the type of Listerial protein desired in the fusion protein and will be readily apparent to those skilled in the art of *Listeria* molecular biology. For example, preferred *L. monocytogenes* promoter/regulatory and/or signal sequences which may be used to direct expression of a fusion protein include, but are not limited to, sequences derived from the *Listeria* hly gene which encodes LLO, the *Listeria* p60 (iap) gene, and the *Listeria* actA gene which encodes a surface protein necessary for *L. monocytogenes* actin assembly. Other promoter sequences of interest include the plcA gene which encodes PI-PLC, the *Listeria* mpl gene, which encodes a metalloprotease, and the *Listeria* inlA gene which encodes internalin, a *Listeria* membrane protein. The heterologous regulatory elements such as promoters derived from phage and promoters or signal sequences derived from other bacterial species may be employed for the expression of a heterologous antigen by the *Listeria* species.

In certain embodiments, the attenuated *Listeria* includes a vector. The vector may include DNA encoding a heterologous antigen. In some instances, the vector is a plasmid that is capable of replication in *Listeria*. The vector may encode a heterologous antigen, wherein expression of the antigen is under the control of eukaryotic promoter/regulatory sequences, e.g., is present in an expression cassette. Typical plasmids having suitable promoters that are of interest include, but are not limited to, pCMVbeta comprising the immediate early promoter/enhancer region of human cytomegalovirus, and those which include the SV40 early promoter region or the mouse mammary tumor virus LTR promoter region.

As such, in certain embodiments, the subject bacteria include at least one coding sequence for heterologous polypeptide/protein, as described above. In some instances, the coding sequence is one that lacks introns, e.g., is a continuous open reading frame that has a sequence which is the same as a cDNA sequence which may be produced from chromosomal sequence. In some embodiments, this coding sequence is part of an expression cassette, which provides for expression of the coding sequence in the *Listeria* cell for which the vector is designed. The term "expression cassette" as used herein refers to an expression module or expression construct made up of a recombinant DNA molecule containing at least one desired coding sequence and appropriate nucleic acid sequences necessary for the expression of the operably linked coding sequence in a particular host organism, i.e., the *Listeria* cell for which the vector is designed, such as the promoter/regulatory/signal sequences identified above, where the expression cassette may include coding sequences for two or more different polypeptides, or multiple copies of the same coding sequence, as desired. As such, the size of the encoded product may vary greatly, and a broad spectrum of different products may be encoded by the expression cassettes present in the vectors of this embodiment.

As indicated above, the vector may include at least one coding sequence, where in certain embodiments the vectors include two or more coding sequences, where the coding sequences may encode products that act concurrently to provide a desired results. In general, the coding sequence may encode any of a number of different products and may be of a variety of different sizes, where the above discussion merely provides representative coding sequences of interest.

Utility

The above-described bacteria find use in a number of different applications. Representative uses of the subject bacteria include, but are not limited to: (a) immunogens for generating antibodies to *Listeria* spp.; (b) adjuvant compositions in immunizing protocols; (c) vectors for introducing macromolecules, e.g., nucleic acids or proteins, into the cytoplasm of target cells; and (d) vaccine compositions, e.g., for eliciting or boosting a cellular immune response in a host. Each of these representative applications is now further described separately below. Uses for attenuated *Listeria* spp. are also described in U.S. Pat. Nos. 8,679,476; 8,277,797; 8,192,991; 7,842,289; 7,794,728; 7,749,510; 7,488,487; 7,425,449; 6,599,502; 6,504,020; 6,287,556; 6,099,848; 6,004,815; 5,830,702; and 5,643,599; the disclosures of which applications are herein incorporated by reference.

Vaccines

The subject bacteria find use as vaccines. The vaccines of the present invention are administered to a vertebrate by contacting the vertebrate with a sub-lethal dose of the attenuated *Listeria* vaccine, where contact typically includes administering the vaccine to the host. In some embodiments, the bacteria are provided in a pharmaceutically acceptable formulation. Administration can be oral, parenteral, intranasal, intramuscular, intradermal, intraperitoneal, intravascular, subcutaneous, direct vaccination of lymph nodes, administration by catheter or any one or more of a variety of well-known administration routes. In farm animals, for example, the vaccine may be administered orally by incorporation of the vaccine in feed or liquid (such as water). It may be supplied as a lyophilized powder, as a frozen formulation or as a component of a capsule, or any other convenient, pharmaceutically acceptable formulation that preserves the antigenicity of the vaccine. Any one of a number of well-known pharmaceutically acceptable diluents or excipients may be employed in the vaccines of the invention. Suitable diluents include, for example, sterile, distilled water, saline, phosphate buffered solution, and the like. The amount of the diluent may vary widely, as those skilled in the art will recognize. Suitable excipients are also well known to those skilled in the art and may be selected, for example, from A. Wade and P. J. Weller, eds., *Handbook of Pharmaceutical Excipients* (1994) The Pharmaceutical Press: London. The dosage administered may be dependent upon the age, health and weight of the patient, the type of patient, and the existence of concurrent treatment, if any. The vaccines can be employed in dosage forms such as capsules, liquid solutions, suspensions, or elixirs, for oral administration, or sterile liquid for formulations such as solutions or suspensions for parenteral, intranasal intramuscular, or intravascular use. In accordance with the invention, the vaccine may be employed, in combination with a pharmaceutically acceptable diluent, as a vaccine composition, useful in immunizing a patient against infection from a selected organism or virus or with respect to a tumor, etc. Immunizing a patient means providing the patient with at least some degree of therapeutic or prophylactic immunity against selected pathogens, cancerous cells, etc.

The subject vaccines find use in methods for eliciting or boosting a cellular immune response, e.g., a helper T cell or a cytotoxic T-cell response to a selected agent, e.g., pathogenic organism, tumor, etc., in a vertebrate, where such methods include administering an effective amount of the *Listeria* vaccine. The subject vaccines find use in methods for eliciting in a vertebrate an innate immune response that augments the antigen-specific immune response. Furthermore, the vaccines of the present invention may be used for treatment post-exposure or post diagnosis. In general, the use of vaccines for post-exposure treatment would be recognized by one skilled in the art, for example, in the treatment of rabies and tetanus. The same vaccine of the present invention may be used, for example, both for immunization and to boost immunity after exposure. Alternatively, a different vaccine of the present invention may be used for post-exposure treatment, for example, such as one that is specific for antigens expressed in later stages of exposure. As such, the subject vaccines prepared with the subject vectors find use as both prophylactic and therapeutic vaccines to induce immune responses that are specific for antigens that are relevant to various disease conditions.

The patient may be any human and non-human animal susceptible to infection with the selected organism. The subject vaccines will find particular use with vertebrates such as man, and with domestic animals. Domestic animals include domestic fowl, bovine, porcine, ovine, equine, caprine, Leporidate (such as rabbits), or other animal which may be held in captivity.

The subject vaccines find use in vaccination applications as described in PCT Published Application Nos.: WO 2014/106123; WO 2014/074635; WO 2009/143085; WO 2008027560 WO 2008066774; WO 2007117371; WO 2007103225; WO 2005071088; WO 2003102168; WO 2003/092600; WO/2000/009733; and WO 1999/025376; the disclosures of which applications are herein incorporated by reference.

Generation of *Listeria* Specific Antibodies

The subject bacteria find use in the generation of antibodies specific for *Listeria* spp. In these applications, the bacteria are administered to a suitable host according to known techniques, and resultant antibodies are harvested from the immunized host. Immunization can be carried out in a variety of ways with a number of different animals. Host animals of interest include rabbits, mice, rats, goats and sheep, etc. Any mammal capable of immune response can be employed as the host animal in antibody production. For the most part for commercial production of antibodies, relatively large animals are employed, such as equine, bovine, porcine, canine, ovine, caprine, rodentia, rabbits and hares. A representative antibody production protocol in which the subject attenuated bacteria may be employed includes the antibody generation protocol as described in U.S. Pat. No. 4,816,253; the disclosure of which is herein incorporated by reference.

Adjuvant Composition

The subject bacterial strains also find use as immunopotentiating agents, i.e., as adjuvants. In such applications, the subject attenuated bacteria may be administered in conjunction with an immunogen, e.g., a tumor antigen, modified tumor cell, etc., according to methods known in the art where live bacterial strains are employed as adjuvants. See, e.g., Berd et al., Vaccine 2001 Mar. 21; 19(17-19):2565-70.

In some embodiments, the bacterial strains are employed as adjuvants by chemically coupled to a sensitizing antigen. The sensitizing antigen can be any antigen of interest, where representative antigens of interest include, but are not limited to: viral agents, e.g., Herpes simplex virus; malaria parasite; bacteria, e.g., *staphylococcus aureus* bacteria, diphtheria toxoid, tetanus toxoid, shistosomula; tumor cells, e.g. $CAD_2$ mammary adenocarcinomia tumor cells, and hormones such as thyroxine $T_4$, triiiodothyronine $T_3$, and cortisol. The coupling of the sensitizing antigen to the immunopotentiating agent can be accomplished by means of various chemical agents having two reactive sites such as, for example, bisdiazobenzidine, glutaraldehyde, di-iodoacetate, and diisocyanates, e.g., m-xylenediisocyanate and toluene-2,4-diisocyanate. Use of *Listeria* spp. as adjuvants is further described in U.S. Pat. No. 4,816,253; the disclosure of which is herein incorporated by reference.

Delivery Vehicles

The subject bacteria also find use as vectors or delivery vehicles for delivery of macromolecules into target cells, e.g., as described in: PCT publication no. WO 00/09733 (the disclosure of which is herein incorporated by reference); and Dietrich et al., Nature Biotechnology (1998) 16: 181-185. A variety of different types of macromolecules may be delivered, including, but not limited to: nucleic acids, polypeptides/proteins, etc., as described in these publications.

The following examples are offered by way of illustration and not by way of limitation.

Experimental

I. Materials and Methods

A. Bacterial Strains and Growth Conditions

All *L. monocytogenes* strains used and generated in this study were in the 10403S background and are listed (Table 1).

TABLE 1

*Listeria monocytogenes* strains used in this study.

| Strain | Strain# | Description | Source |
|---|---|---|---|
| 10403S | — | Wild type (WT) *Listeria monocytogenes* strain | (1) |
| ΔsecA2 | DP-L4342 | In frame deletion of lmo0583 | (2) |
| ΔpgdAΔcatA | DP-L5220 | In frame deletion of lmo0415 and lmo1291 | (3) |
| Δtap | DP-L4611 | In frame deletion of lmo0582 | (4) |
| Δlmo2769 | DP-L6209 | In frame deletion of lmo2769 | This study |
| Δlmo2769ΔsecA2 | DP-L6210 | In frame deletion of lmo2769 in a ΔsecA2 background | This study |
| Δlmo2769ΔsecA2 + pPL2:2767-2769 | DP-L6211 | Δlmo2769ΔsecA2strain complemented with pPL2 lmo2767-2769 construct | This study |
| R57 + pPL2:2767-2769 | DP-L6212 | R57 strain complemented with pPL2 lmo2767-2769 construct | This study |
| lmo2768::Tn | DP-L6155 | HimarI Transposon insert in lmo2768 | (5) |
| ΔsecA2:lmo2768::Tn | DP-L6213 | HimarI Transposon insert in lmo2768 in ΔsecA2 strain | This study |
| Δlmo1721 | DP-L6214 | In frame deletion of lmo1721 | This study |
| Δlmo1721ΔsecA2 | DP-L6215 | In frame deletion of lmo1721 in a ΔsecA2 background | This study |
| Δlmo2769Δlmo1721 | DP-L6216 | In frame deletion of lmo1721 in a Δlmo2769 background | This study |
| Δlmo2769Δlmo1721ΔsecA2 | DP-L6217 | In frame deletion of lmo1721 in a Δlmo2769ΔsecA2 background | This study |
| ΔsecA2:lmo2637::Tn | DP-L6218 | HimarI Transposon insert in lmo2637 in ΔsecA2 strain | This study |
| ΔsecA2prlA1 | DP-L6219 | HimarI Transposon insert in lmo2637 in ΔsecA2 strain with secY (G408R) | This study |
| WT:lmo2637::Tn | DP-L6220 | HimarI Transposon insert in lmo2637 in 10403S (WT) strain | Lab collection |
| prlA1 | DP-L6221 | HimarI Transposon insert in lmo2637 in WT strain with secY (G40SR) | This study |
| Δlmo2769ΔsecA2:bno2637::Tn | DP-L6222 | HimarI Transposon insert in lmo2637 in Δlmo2769ΔsecA2 strain with WT secY | This study |
| Δlmo2769ΔsecA2prlA1 | DP-L6223 | HimarI Transposon insert in lmo2637 in Δlmo2769ΔsecA2 strain with secY (G408R) | This study |
| Δlmo1721ΔsecA2prlA1 | DP-L6224 | HimarI Transposon insert in lmo2637 in Δlmo1721ΔsecA2 strain with secY (G408R) | This study |
| Δlmo2769Δlmo1721ΔsecA2:Tn | DP-L6225 | HimarI Transposon insert in lmo2637 in Δlmo2769Δlmo1721ΔsecA2 strain with WT secY | This study |
| Δlmo2769Δlmo1721ΔsecA2prlA1 | DP-L6226 | HimarI Transposon insert in lmo2637 in Δlmo2769Δlmo1721ΔsecA2 strain with secY (G408R) | This study |
| R57prlA1 | DP-L6227 | HimarI Transposon insert in lmo2637 in strain R57 with the secY (G408R) | This study |

TABLE 1-continued

Listeria monocytogenes strains used in this study.

| Strain | Strain# | Description | Source |
|---|---|---|---|
| R57:lmo2637:Tn | DP-L6228 | HimarI Transposon insert in lmo2637 in strain R57 with WT secY | This study |

The ΔsecA2 previously characterized (Lenz et al., "SecA2-dependent secretion of autolytic enzymes promotes *Listeria monocytogenes* pathogenesis," Proc. Nat'l Acad. Sci USA (2003) 100:12432-12437; Lenz & Portnoy "Identification of a second *Listeria* secA gene associated with protein secretion and the rough phenotype," Mol. Microbiol (2002) 45:1043-1056) served as a parent strain for generating motility revertants. Unless otherwise stated all *L. monocytogenes* strains were grown in brain heart infusion medium (BHI, Difco, Detroit, Mich.). All *E. coli* strains used for generating in-frame deletion and complement constructs were grown in Luria-Bertani (LB, Difco, Detroit, Mich.) medium.

B. Swarming Motility

A single colony of ΔsecA2 was used to generate a single motility revertant by stab-inoculating semi-solid LB 0.4% agar at 30° C. for five days. Revertant strains were grown overnight in BHI broth at 30° C. without shaking, 1 µL of culture was then incorporated into a semi-solid LB agar and swarming area was evaluated using ImageJ (available at the website produced by placing "http://" before rsweb.nih.gov/ij/") following incubation at 30° C. for 48 h.

C. L2 Plaque Assay

Plaque assays using murine L2 fibroblasts were performed as previously described (Sun et al., "Isolation of *Listeria monocytogenes* small-plaque mutants defective for intracellular growth and cell-to-cell spread," Infect. Immun. (1990) 58:3770-3778). Briefly, overnight 30° C. static cultures of *L. monocytogenes* were allowed to infect monolayers of L2 cells for 1 h. Cells were washed and overlaid with 0.7% agarose in DMEM (Gibco/Invitrogen, CA) containing 10 µg/mL gentamycin (GM). After 3 days at 37° C., plaques were overlaid with 2 mL of 0.7% agarose in DMEM with GM and 0.3% neutral red (Sigma-Aldrich). Monolayers were stained overnight and plaque size was evaluated using ImageJ.

D. DNA Isolation and Sequencing

Genomic DNA was isolated from stationary phase cultures of *L. monocytogenes* using the MasterPure DNA purification kit (Epicentre). DNA was then fragmented using Covaris S22 (Covaris Inc.). Libraries were constructed using Apollo 324 (IntegenX Inc.), PCR amplified, and multiplexed at the Vincent J. Coates Genomics Sequencing Laboratory at UC Berkeley. The resulting libraries were sequenced using single-end reads with a HiSeq 2000 Illumina platform. Sequence data were aligned to the *L. monocytogenes* 10403S reference genome CP002002 using Bowtie 2 (Langmead & Salzberg, "Fast gapped-read alignment with Bowtie 2," Nat. Methods (2012) 9:357-359) and SNPs were identified using SAM tools (Li et al., "The sequence slignment/map format and SAMtools," Bioinformatics (2009) 25:2078-2079). Approximately 93% of all reads aligned to the reference genome, resulting in >50x coverage.

E. In-Frame Deletion and Complementation Constructs

In-frame deletion mutants of lmo2769 and lmo1721 were constructed by splice overlap extension and introduced by allelic exchange using pKSV7 using JD17-JD20 and JD30-JD33 primers, respectively (Table 2) as previously described (Camilli et al. "Dual roles of plcA in *Listeria monocytogenes* pathogenesis," (1993) Mol. Microbiol 8:143-157).

TABLE 2

Deletion and Complement Primer Sequences

| Primer | 5'-3 Sequence | Description |
|---|---|---|
| JD17 | ATTAGTCGACCTCGGAGTTTGGTGTCTTCTGG (SEQ ID NO: 01) | lmo2769 deletion primer A |
| JD18 | ATTACTGCAGAAACGATGCGGACTCAAACG (SEQ ID NO: 02) | lmo2769 deletion primer D |
| JD19 | CTCCCGTCTGTTTTAAATCTCGTATTTAGTTAAGTTCCG AATTTTCAT (SEQ ID NO: 03) | lmo2769 deletion primer B |
| JD20 | ATGAAAATTCGGAACTTAACTAAATACGAGATTTAAAAC AGACGGGAG (SEQ ID NO: 04) | lmo2769 deletion primer C |
| JD30 | ATTAGTCGAC ACAGATGTAGCGGCTCGTGG (SEQ ID NO: 05) | lmo1721 deletion primer A |
| JD31 | GATTCCTTTTCTTAATTTTCTTCGACTTCTTCTTTTCTA CTAGACAT (SEQ ID NO: 06) | lmo1721 deletion primer B |
| JD32 | ATGTCTAGTAGAAAAGAAGAAGTCGAAGAAAATTAAGA AAAAGGAATC (SEQ ID NO: 07) | lmo1721 deletion primer C |
| JD33 | ATTACTGCAGCGCCGTCCATTGTTCCATAG (SEQ ID NO: 08) | lmo1721 deletion primer D |

TABLE 2-continued

Deletion and Complement Primer Sequences

| Primer | 5'-3 Sequence | Description |
|---|---|---|
| JD46 | ATTAGTCGACCTGGATGTGGCGTAAGGG (SEQ ID NO: 09) | lmo2769-lmo2767 F' primer |
| JD47 | ATTAGGATCCCATAACTTTGTCCCGATTGTCC (SEQ ID NO: 10) | lmo2769-lmo2767 R' primer |

The pPL2 integration vector was used to complement Δlmo2769 mutants and R57 revertant strain with the lmo2769-2767 operon and all the endogenous regulatory sequences using JD46-JD47 primers (Table 2) as previously described (Lauer et al., "Construction, characterization, and use of two Listeria monocytogenes site-specific phage integration vectors," J. Bacteriol. (2002) 184:4177-4186).

F. Transductions

Transductions of the lmo2768::Tn and lmo2637::Tn donor strains were generated using phage U153 and erythromycin as a selection marker, as previously described (Hodgson D A, "Generalized transduction of serotype 1/2 and serotype 4b strains of Listeria monocytogenes," Mol. Microbiol. (2000) 35:312-323). Strain R57 containing the prlA1 was used as the recipient strain for lmo2637::Tn and subsequent recipient strains of secY mutation were confirmed by Sanger sequencing (Elim Biopharmaceuticals, Hayward, Calif.).

G. In Vivo Mouse Infections

CD1 (Crl:CD1(ICR)) mice (Charles River Laboratories) were injected intravenously with $1\times10^5$ CFU of wild-type or mutant L. monocytogenes strains. Spleens and livers were harvested after 48 h and bacterial burdens were evaluated as previously described (Witte et al., "Cyclic di-AMP is critical for Listeria monocytogenes growth, cell wall homeostasis, and establishment of infection," mBio (2013) 4:e00282-00213).

H. Disk Diffusion Assay

A total of $3\times10^8$ stationary phase L. monocytogenes cells were plated on BHI agar plates. Sterile Whatman paper discs (7 mm in diameter) containing 1 mg of chicken egg white lysozyme (Sigma), 10 μg of vancomycin or 120 μg of penicillin in 10 μL volume were added to plates. The area of growth inhibition around each disc was measured using ImageJ following 24 hr incubation at 37° C.

I. Microscopy

Phase contrast microscopy was performed using stationary BHI culture at 37° C. Fluorescence microscopy was conducted using Olympus IX81 TIRF microscope on mid-log cells stained with SYTO9 green fluorescent stain (Invitrogen).

J. Western Blotting

Secreted proteins from mid-log LB culture supernatants were precipitated with 10% trichloro-acetic acid (TCA), as previously described (Zemansky et al., "Development of a mariner-based transposon and identification of Listeria monocytogenes determinants, including the peptidyl-prolyl isomerase PrsA2, that contribute to its hemolytic phenotype," J. Bacteriol. (2009) 191:3950-3964) and solubilized in NuPAGE LDS buffer (Invitrogen) containing 5% β-mercaptoethanol at a volume adjusted to $OD_{600}$ for each strain. Samples were fractionated by SDS-PAGE, transferred to a PVDF membrane for immunoblotting with polyclonal anti-P60 antibodies and quantified using the Odyssey infrared imaging system (LI-COR Biosciences).

II. Results:

A. Isolation and Initial Characterization of ΔsecA2 Suppressor Mutants

The inability of bacteria to properly septate during cell division can negatively influence swarming efficiency in semisolid media (Blackman et al., "The role of autolysins during vegetative growth of Bacillus subtilis 168," Micobiology (1998) 144:73-82; Halbedel et al., "DivIVA affects secretion of virulence-related autolysins in Listeria monocytogenes," Mol. Microbiol. (2012) 83:821-839; Rashid et al., "Bacillus subtilis mutant deficient in the major autolytic amidase and glucosaminidase is impaired in motility," FEMS Microbiol. Lett. (1993) 112:135-140). Indeed, the filamentous nature of the L. monocytogenes secA2 mutant led to a 92% reduction in swarming motility compared to the wild type (WT) 10403S strain (FIG. 1). Seventy spontaneous, independent ΔsecA2 suppressor mutants were generated by identifying swarming bacteria that appeared after five days incubation at 30° C. in semisolid LB agar. These suppressor mutants displayed a wide range of swarming phenotypes (11 to 112%) when compared to the WT strain (FIG. 1). Motility revertants were further characterized based on their colony and microscopic appearance (Table 3).

TABLE 3

Colony and microscopic morphology of ΔsecA2 revertants.

| Strain | Colony | Chaining# | Lyzozyme$ |
|---|---|---|---|
| R1 | smooth | + | 1.79 (±0.10) |
| R2 | rough | ++++ | 1.64 (±0.10) |
| R3.1 | smooth | + | 1.71 (±0.00) |
| R3.2 | rough | ++++ | 1.71 (±0.20) |
| R4 | smooth | + | 1.64 (±0.10) |
| R5 | smooth | ++ | 1.71 (±0.00) |
| R6 | rough | +++ | 1.57 (±0.00) |
| R7 | smooth | + | 2.36 (±0.10) |
| R8 | rough | +++ | 2.50 (±0.10) |
| R9 | rough | +++ | 2.17 (±0.30) |
| R10.1 | smooth | ++ | 1.71 (±0.00) |
| R10.2 | rough | +++ | 1.86 (±0.00) |
| R11 | smooth | ++ € | 1.86 (±0.00) |
| R12 | smooth | ++ | 2.29 (±0.00) |
| R13 | rough | +++ | 1.64 (±0.10) |
| R14 | rough | +++ | 1.93 (±0.10) |
| R15 | rough | +++ | 1.86 (±0.00) |
| R16 | smooth | + | 1.71 (±0.00) |
| R17 | smooth | ++ € | 1.71 (±0.00) |
| R18.1 | smooth | + € | 1.71 (±0.00) |
| R18.2 | rough | ++++ | 1.64 (±0.10) |
| R19 | rough | ++++ | 1.79 (±0.10) |
| R20 | rough | +++ | 1.79 (±0.10) |
| R21 | smooth | ++ | 1.93 (±0.10) |
| R22 | rough | +++ | 1.79 (±0.10) |
| R23 | smooth | + | 2.10 (±0.40) |
| R24 | smooth | + € | 2.14 (±0.20) |
| R25 | rough | ++++ | 1.64 (±0.10) |
| R26 | smooth | + € | 2.93 (±0.30) |
| R27 | rough | +++ | 1.64 (±0.10) |
| R28 | smooth | ++ | 1.71 (±0.00) |
| R29 | smooth | + | 1.71 (±0.20) |

TABLE 3-continued

Colony and microscopic morphology of ΔsecA2 revertants.

| Strain | Colony | Chaining[#] | Lyzozyme[$] |
|---|---|---|---|
| R30 | smooth | + | 3.36 (±0.10) |
| R31 | rough | +++ | 1.79 (±0.10) |
| R32 | smooth | ++ € | 1.64 (±0.10) |
| R33 | rough | +++ | 1.71 (±0.00) |
| R34 | smooth | ++ € | 2.67 (±0.20) |
| R35 | smooth | ++ | 2.67 (±0.60) |
| R36 | smooth | + | 1.64 (±0.10) |
| R37 | smooth | ++ | 1.71 (±0.00) |
| R38 | smooth | ++ | 1.57 (±0.00) |
| R39 | rough | ++++ | 2.00 (±0.20) |
| R40 | rough | +++ € | 1.79 (±0.10) |
| R41 | smooth | + | 1.79 (±0.10) |
| R42 | smooth | + | 2.14 (±0.20) |
| R43 | rough | +++ | 1.57 (±0.20) |
| R44 | smooth | + | 2.21 (±0.30) |
| R45 | smooth | + | 2.29 (±0.20) |
| R46 | smooth | + | 2.50 (±0.10) |
| R47.1 | smooth | + | 2.57 (±0.00) |
| R47.2 | rough | +++ | 2.64 (±0.10) |
| R48 | smooth | + | 1.71 (±0.00) |
| R49 | smooth | ++ | 1.71 (±0.20) |
| R50 | smooth | ++ | 2.21 (±0.10) |
| R51 | rough | + | 1.71 (±0.00) |
| R52 | smooth | + | 1.64 (±0.20) |
| R53 | smooth | + | 2.29 (±0.20) |
| R54 | smooth | ++ | 2.57 (±0.20) |
| R55 | rough | +++ | 1.86 (±0.40) |
| R56 | smooth | ++ | 2.14 (±0.00) |
| R57 | smooth | + | 2.87 (±0.40) |
| R58 | smooth | + | 1.86 (±0.20) |
| R59 | smooth | + | 1.79 (±0.10) |
| R60.1 | smooth | ++ | 2.49 (±0.20) |
| R60.2 | rough | +++ | 1.71 (±0.00) |
| R61 | smooth | + | 2.29 (±0.20) |
| R62 | smooth | ++ | 2.50 (±0.10) |
| R63.1 | smooth | ++ | 2.21 (±0.10) |
| R63.2 | rough | +++ | 2.21 (±0.10) |
| R64 | smooth | + € | 3.00 (±0.20) |

[#]Microscopy was conducted on stationary phase cells grown in BHI at 37° C. Chaining phenotype was scored from + to ++++, where WT = + and ΔsecA2 = ++++ according to the following algorithm:
+ = single cells and chains of up to 3 cells/field ×40 magnification
++ = single cells and chains of up to 4 cells/field ×40 magnification
+++ = chains of up to 6 cells/field ×40 magnification
++++ = chains of >6 cells/field ×40 magnification
€ Pleomorphic cells
[$]Disk diffusion susceptibility to 1 mg of lysozyme expressed as ratio of WT, where a ratio >1 indicates increased susceptibility. Values in parenthesis represent standard deviations.

The majority of suppressor mutants (64%) reverted from a rough to a smooth colony morphology. Rough colony morphology correlated with chaining, with less chaining observed for isolates forming smooth colonies. Whereas WT (42-44) and secA2 mutants of *L. monocytogenes* are lysozyme resistant, all 70 suppressor mutants were susceptible to lysozyme (Table 3).

Figure 2:
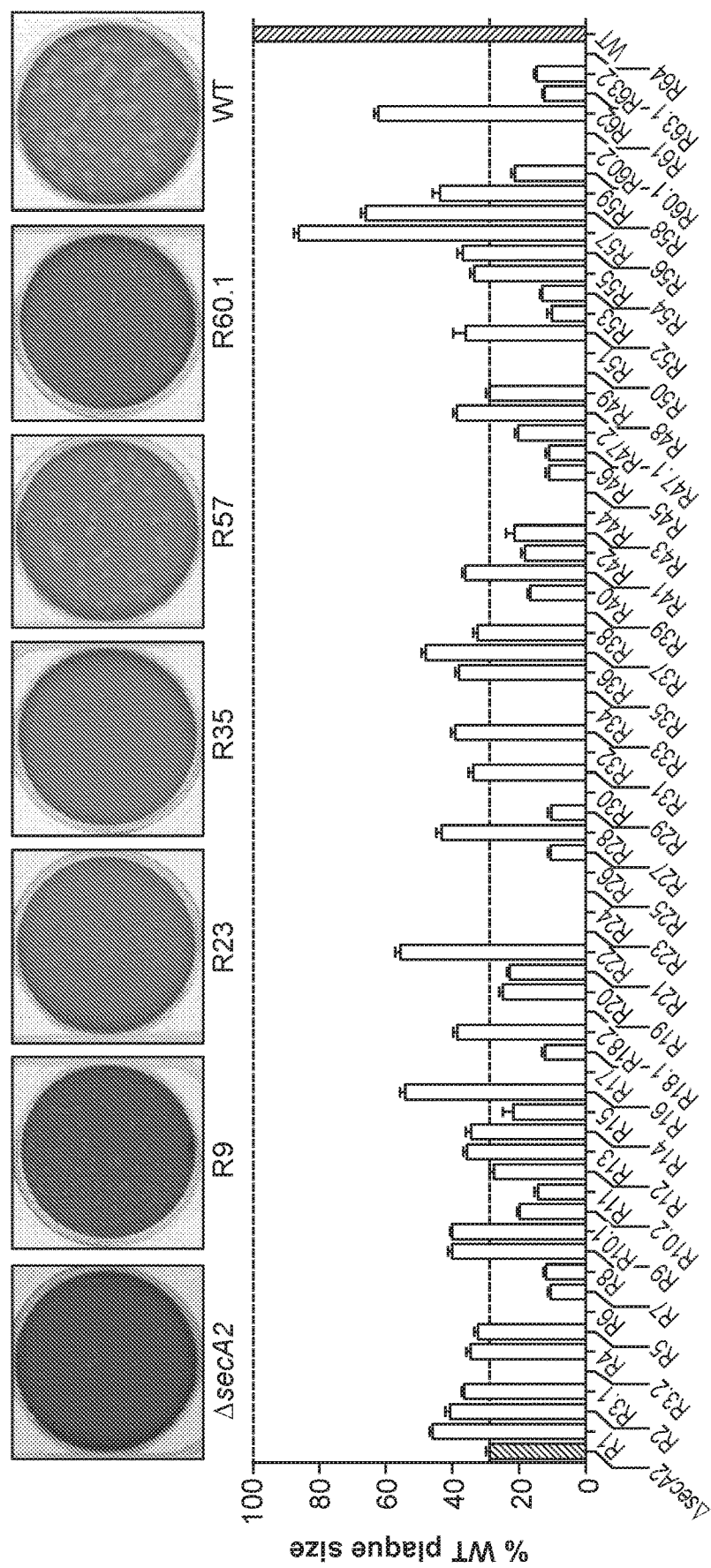
FIG. 2: Plaque size of secA2 suppressor mutants. L2 fibroblasts were infected with secA2 suppressor mutants and mean plaque size was measured 3 days post infection. Plaque area of each mutant is shown as a percentage compared to WT strain. Error bars represent standard deviations of the mean zone ratio between three independent experiments. Images show plaques for the suppressor mutants indicated.

A critical aspect of *L. monocytogenes* pathogenesis is the capacity to spread from cell-to-cell and form plaques in monolayers of tissue culture cells, which correlates well with mouse virulence (Roche et al., "Assessment of the virulence of *Listeria monocytogenes*: agreement between a plaque-forming assay with HT-29 cells and infection of immunocompetent mice," Int. J. Food Microbiol. (2001) 68:33-44). The secA2 mutant forms plaques that are approximately 30% of WT (FIG. 2 and (Lenz et al., "SecA2-dependent secretion of autolytic enzymes promotes *Listeria monocytogenes* pathogenesis," Proc. Nat'l Acad. Sci. USA (2003) 100:12432-12437)). The ΔsecA2 swarming suppressor mutants varied greatly in their ability to form plaques, ranging from 0% to 87% of WT (FIG. 2). There was no significant correlation between chaining phenotype and plaque size, suggesting that chaining alone does not directly influence cell-to-cell spread as measured by the plaque assay.

B. Whole-Genome Sequencing of Five ΔsecA2 Suppressor Mutants

To identify mutations responsible for the observed phenotypes, five strains were selected for further analysis (Table 4).

TABLE 4

Strains selected for sequencing and their phenotypes.

| Strain | Colony | Chaining[€] | Motility[¥] | Plaque[£] |
|---|---|---|---|---|
| R9 | Rough | +++ | 29% (±3) | 41% (±9) |
| R23 | Smooth | + | 55% (±13) | 0% |
| R35 | Smooth | ++ | 102% (±26) | 0% |
| R57 | Smooth | + | 112% (±15) | 87% (±13) |
| R60.1 | Smooth | ++ | 87% (±23) | 21% (±6) |
| ΔsecA2[#] | Rough | ++++ | 9% (±2) | 29% (±9) |

[#]Parent ΔsecA2 was included as a reference strain
[€] Chaining scores interpretation by phase microscopy
+ = single cells and chains of up to 3 cells/field × 40 magnification
++ = single cells and chains of up to 4 cells/field × 40 magnification
+++ = chains of up to 6 cells/field × 40 magnification
++++ = chains of >6 cells/field × 40 magnification
[¥]Expressed as an average percentage (standard deviation) of the swarming area normalized to WT strain on 0.4% LB after 48 h at 30° C.
[£]Expressed as an average percentage (standard deviation) of plaque area of WT strain Whole-genome sequencing revealed a number of single-nucleotide polymorphisms (SNP) that differed from the WT strain and confirmed that each lacked the secA2 gene (Table 5).

TABLE 5

Single-nucleotide polymorphisms (SNP) of strains sequenced.

| Strain | Position | Reference | Alteration | Change | Lmo no. | Gene name | Encoded protein or function |
|---|---|---|---|---|---|---|---|
| R9 | 1104029 | C | T | A141V | lmo1087 | | Ribitol-5-phosphate 2-dehydrogenase |
| | 1921584 | T | C | V195 silent | lmo1892 | pbpA | Penicillin-binding protein 1 |
| | 2812912 | A | G | 48 bp upstream of lmo2769 transcription start site | lmo2769 | | Antibiotic transport system ATP-binding protein |
| R23 | 714441 | A | G | E28G | lmo0699 | fliM | Flagellar motor switch |
| | 2734020 | G | C | G122 silent | lmo2694 | | Lysine decarboxylase |
| | 2811145 | G | T | T169 stop codon | lmo2768 | | Membrane protein (permease) |

TABLE 5-continued

Single-nucleotide polymorphisms (SNP) of strains sequenced.

| Strain | Position | Reference | Alteration | Change | Lmo no. | Gene name | Encoded protein or function |
|---|---|---|---|---|---|---|---|
| R35 | 728791 | G | A | A340T | lmo0714 | fliG | Flagellar motor switch protein G |
| | 736353 | A | G | E176G | lmo0723 | | Methyl-accepting chemotaxis protein |
| | 1102328 | C | T | P499S | lmo1085 | | Similar to teichoic acid biosynthesis protein B |
| | 1191185 | T | C | I486I | lmo1208 | cbiP | Cobyric acid synthase |
| | 1264242 | CTTTTTTTT | CTTTTTTT | 58 bp upstream of lmo1281 transcription start site | lmo1281 | | Hydroxybenzoyl coenzyme A thioesterase |
| | 1343106 | G | A | R232H | lmo1360 | folD | Methylenetetrahydrofolate dehydrogenase/cyclohydrolase |
| | 1390074 | GAAAAAAAA | GAAAAAAA | I309S, premature stop at codon 319 | lmo1403 | mutS | DNA mismatch repair protein MutS |
| | 1932076 | A | G | S247A | lmo1901 | panC | Pantothenate synthetases |
| | 2137030 | A | G | L219W | lmo2100 | | Similar to transcriptional regulator (GntR family) |
| | 2323057 | G | A | R264C | lmo2278 | lysA | L-Alanoyl-D-glutamate peptidase |
| | 2447109 | CAAAAAAA | CAAAAAAA | A25C, premature stop at codon 49 | lmo2421 | | Similar to two-component sensor histidine kinase |
| | 2468643 | CTTTTTTTT | CTTTTTTT | A46Q, premature stop at codon 62 | lmo2444 | | Similar to glycosidase |
| | 2812179 | ATTTTTTT | ATTTTTTT | I229N, premature stop at codon 236 | lmo2769 | | Antibiotic transport system ATP-binding protein |
| R57 | 1738627 | TAA | TAAA | L780F, premature stop at codon 791 | lmo1721 | lacR | Sigma-54 interaction domain-containing protein |
| | 2658496 | C | T | G408R | lmo2612 | secY | Protein translocase subunit SecY |
| | 2812179 | ATTTTTTT | ATTTTTTT | I229N, premature stop at codon 236 | lmo2769 | | Antibiotic transport system ATP-binding protein |
| R60.1 | 311857 | CAAAAAA | CAAAAAA | G109R, premature stop at codon 279 | lmo0290 | wall | Similar to B. subtilis Yycl protein |
| | 2542503 | C | T | D559N | lmo2510 | secA | Protein translocase subunit SecA |
| | 2568428 | T | CA | V211G, premature stop at codon 223 | lmo2537 | mnaA | UDP-N-acetylglucosamine 2-epimerase |

Most revertants encoded three to four SNPs while revertant R35 was an outlier with 13 SNPs, one of which mapped to lmo1403, a gene encoding the DNA mismatch repair protein MutS. We hypothesize that inactivation of mutS led to a hypermutation phenotype (Mérino et al., "A hypermutator phenotype attenuates the virulence of Listeria monocytogenes in a mouse model," Mol. Microbiol (2002) 44:877-887.).

Two revertants, R23 and R35, contained SNPs in genes encoding flagella motor switch proteins FliM and FliG, respectively (Table 5). Both of these proteins function in controlling the direction of flagella rotation (Dyer et al., "A molecular mechanism of bacterial flagellar motor switching," J. Mol. Biol. (2009) 388:71-84; Kihara et al., "Deletion analysis of the flagellar switch protein FliG of Salmonella," J. Bacteriol. (2000) 182:3022-3028; Mariconda et al., "A mechanical role for the chemotaxis system in swarming motility," Mol. Microbiol. (2006) 60:1590-1602; Toker et al., "Deletion analysis of the FliM flagellar switch protein of Salmonella typhimurium," J. Bacteriol. (1996) 178:7069-7079.) and single point mutations in FliM have been shown to restore swarming motility in a chemotaxis deficient mutant of Salmonella enterica (Mariconda et al., id). We hypothesize that SNPs in these genes led to enhanced swarming motility of the corresponding revertants by direct manipulation of the flagella motor. However, neither of these suppressor mutants formed plaques in tissue culture cells and therefore were not subjected to further analysis.

Figure 3:
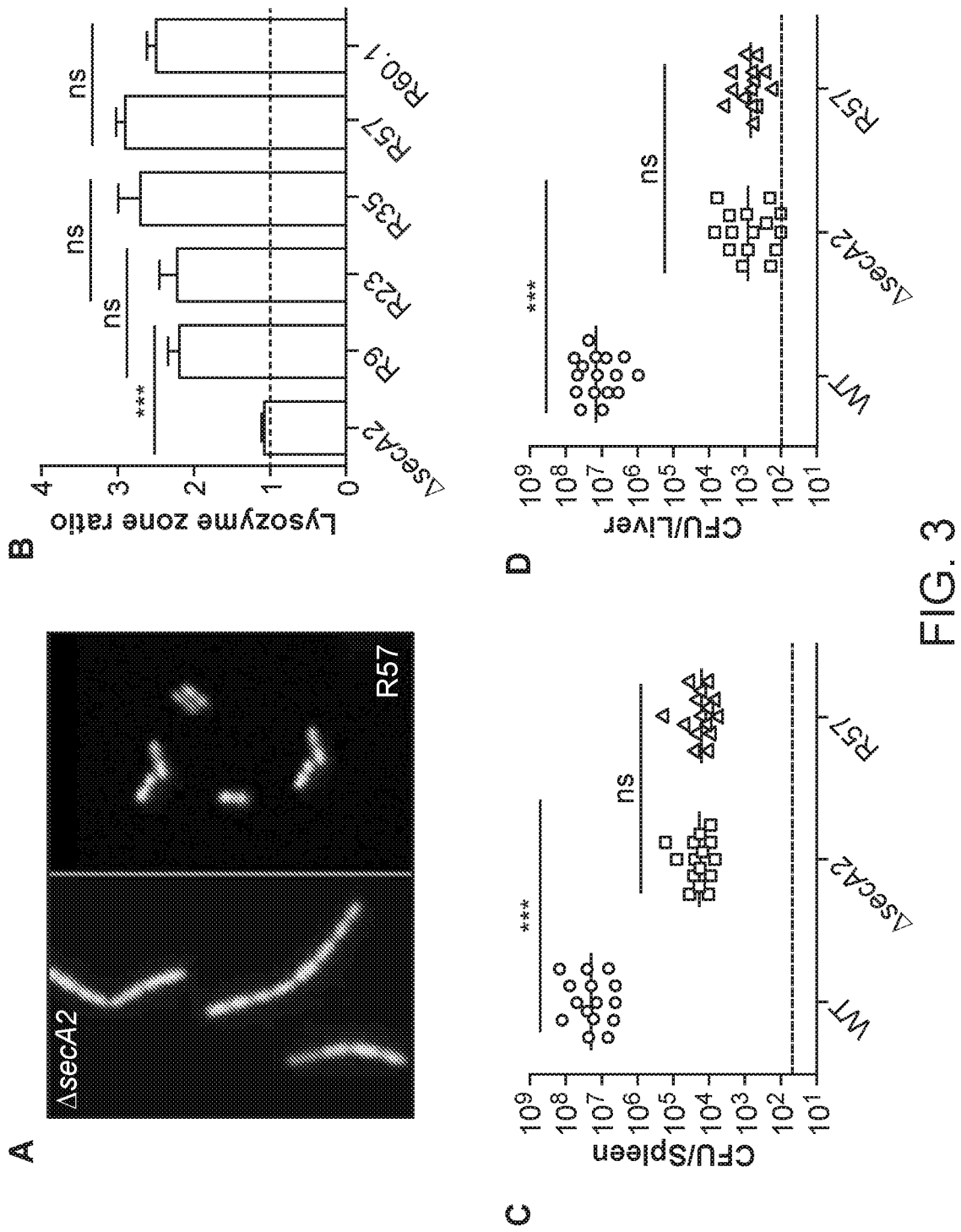
FIGS. 3A-3D: Characterization of the R57 revertant.
Figure 6:
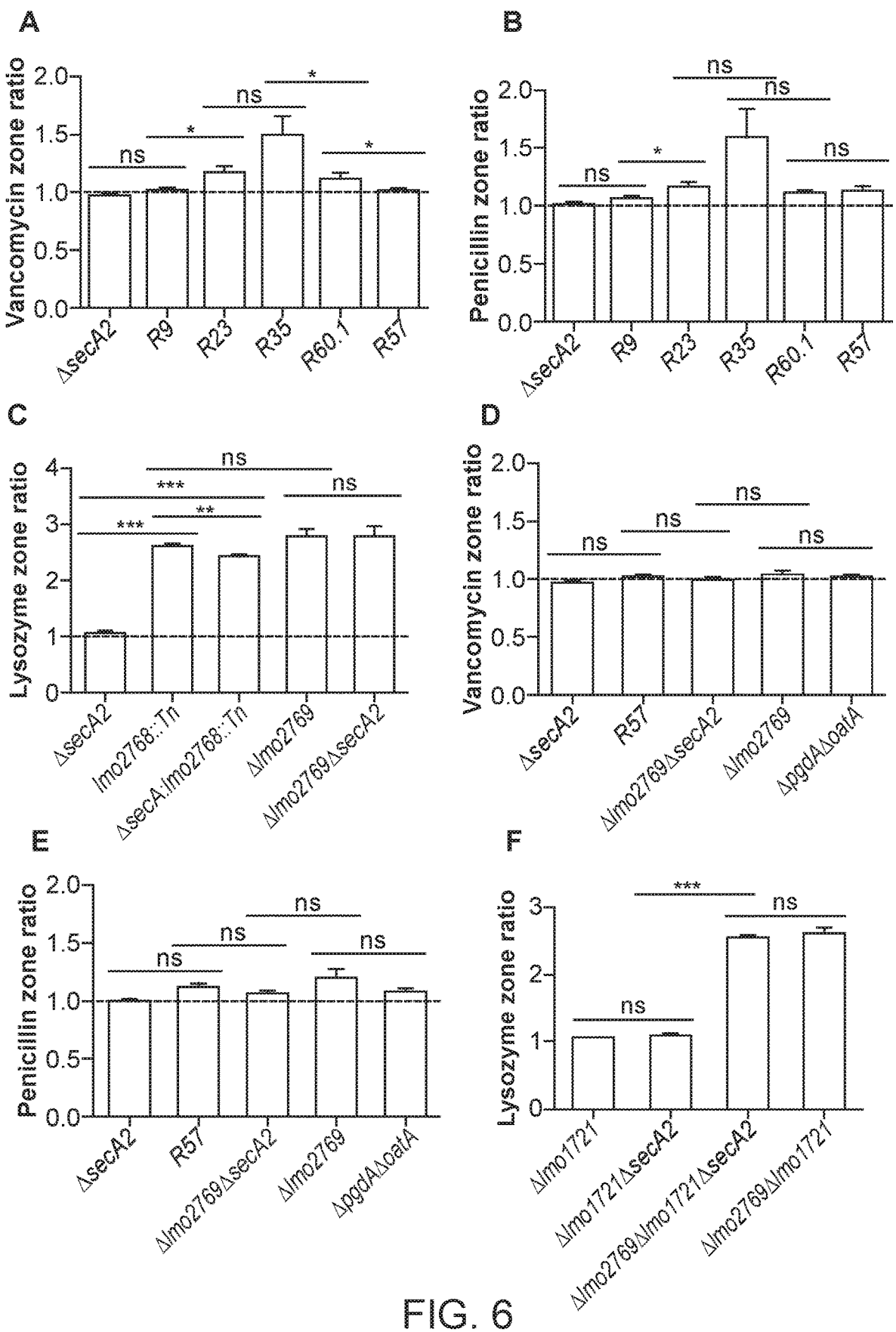
FIGS. 6A-6F.

All suppressor mutants were significantly more susceptible to lysozyme than WT or the parent secA2 mutant strain (FIG. 3B; Table 3). Susceptibility to cell wall-acting antibiotics was less prominent but still evident for R23, R35 and R60.1 (Supplementary FIG. 6A-B). Additionally, four out of five suppressors had mutations in the lmo2769 operon, previously shown to be required for lysozyme resistance (Burke et al., "*Listeria monocytogenes* is resistant to lysozyme by the regulation, not acquisition, of cell wall modifying enzymes," J. Bacteriol. (2014) JB.02053-02014). Lastly, mutant R60.1 contained a mutation in wall, a regulator of the WaIRK two-component system required for autolysin regulation and lysozyme resistance in *L. monocytogenes* (Burke et al., id.).

Most notably, mutants R57 and R60.1 contained SNPs in genes encoding two essential components of the canonical Sec pathway, SecY and SecA, respectively. These mutations resulted in amino acid substitutions leading to altered protein function and the SNP in secY is analyzed in detail below. The identification of mutations in secY and secA shows a link between SecA2 and the general Sec-pathway in *L. monocytogenes*.

Improved swarming motility and lack of chaining did not improve cell-to-cell spread in most of the mutants, with the exception of R57. This mutant showed a complete loss of chaining (FIG. 3A) and restored cell-to-cell spread to 87% of the WT strain (FIG. 1). Based on the increased plaque size, we hypothesized that this strain would show increased virulence in vivo. However, upon intravenous infection of mice, the R57 mutant was just as attenuated as the ΔsecA2 parental strain (FIG. 3C-D). The lack of even a partial rescue of virulence was somewhat surprising and suggested that either the secA2 mutation cannot be overcome in vivo, or that the combination of SNPs resulted in virulence suppression. Because of these prominent phenotypes and a possible link with the SecYEG translocon, R57 was chosen for further analysis.

C. Mutations in the lmo2769 Operon Resulted in Lysozyme Susceptibility and Increased Swarming Motility but did not Contribute to Increased Plaque Formation.

Figure 4:
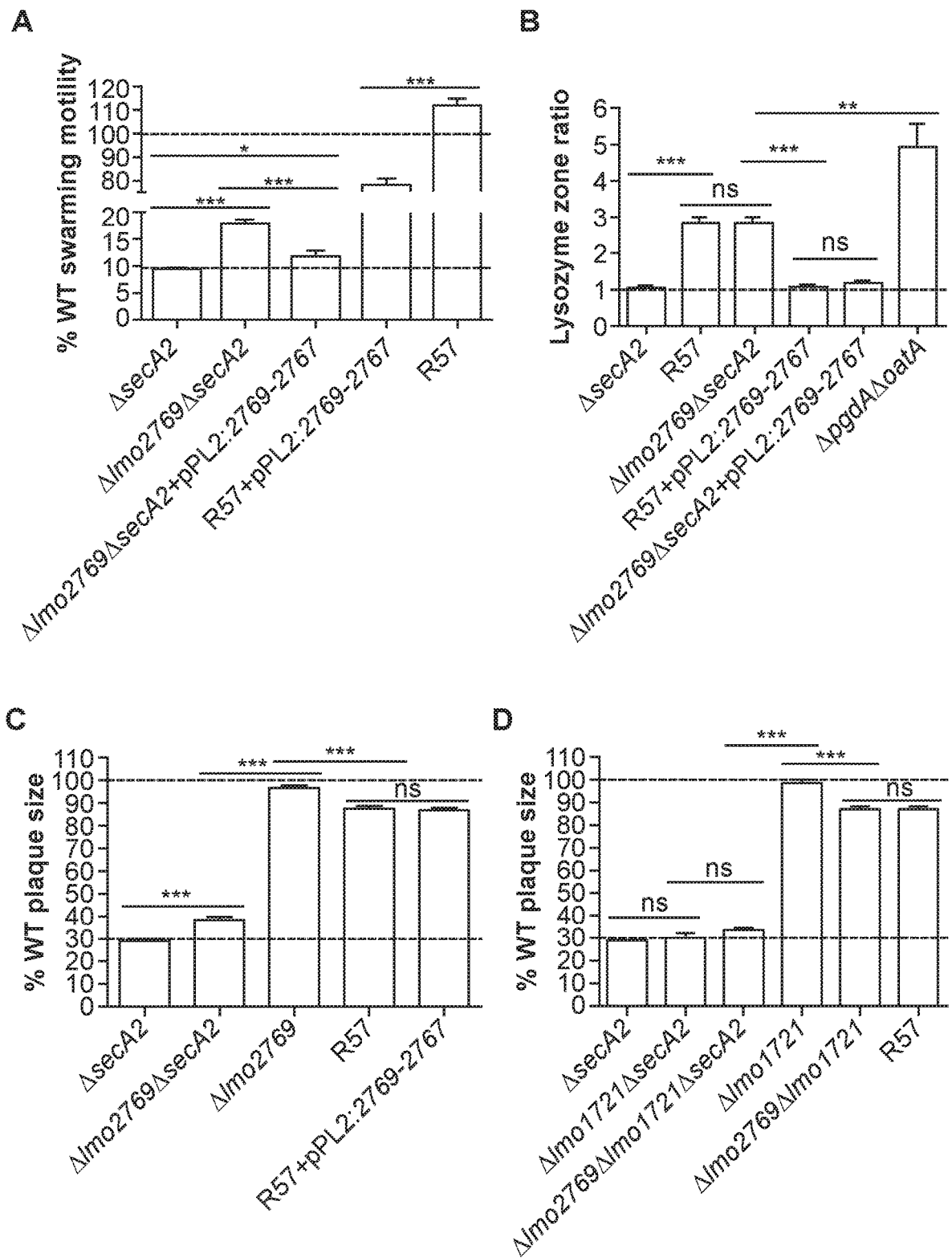
FIGS. 4A-4D: Characterization of lmo2769 mutant in a ΔsecA2 background.

Four out of five sequenced revertants had SNPs in lmo2769 (Table 5). The first gene of this uncharacterized operon, lmo2769, encodes an ATP-binding protein, followed by an ABC transporter permease and a membrane protein encoded by lmo2768 and lmo2767, respectively. The function of the ABC transporter is unknown; however, it has been implicated in lysozyme sensitivity (Burke et al., J Bacteriol. (2014)196:3756-67). It seemed probable that mutations in this operon, in addition to contributing to lysozyme susceptibility, also enhanced swarming motility of ΔsecA2 revertants. Indeed the swarming motility of Δlmo2769ΔsecA2 mutant was twice that of the parent ΔsecA2 strain (FIG. 4A). The Δlmo2769 mutants were also significantly more susceptible to lysozyme than WT or ΔsecA2 (FIG. 4B, FIG. 6 and (Burke et al, id.)). There was no change in susceptibility to other cell wall acting agents tested (FIG. 6), however lmo2768::Tn has been shown to be more susceptible to CAMPs and cefuroxime (Burke et al, id.). The increase in swarming motility and lysozyme susceptibility was diminished by complementing either the Δlmo2769ΔsecA2 double mutant or R57 with the lmo2769 operon (FIG. 4A-B).

Figure 7:
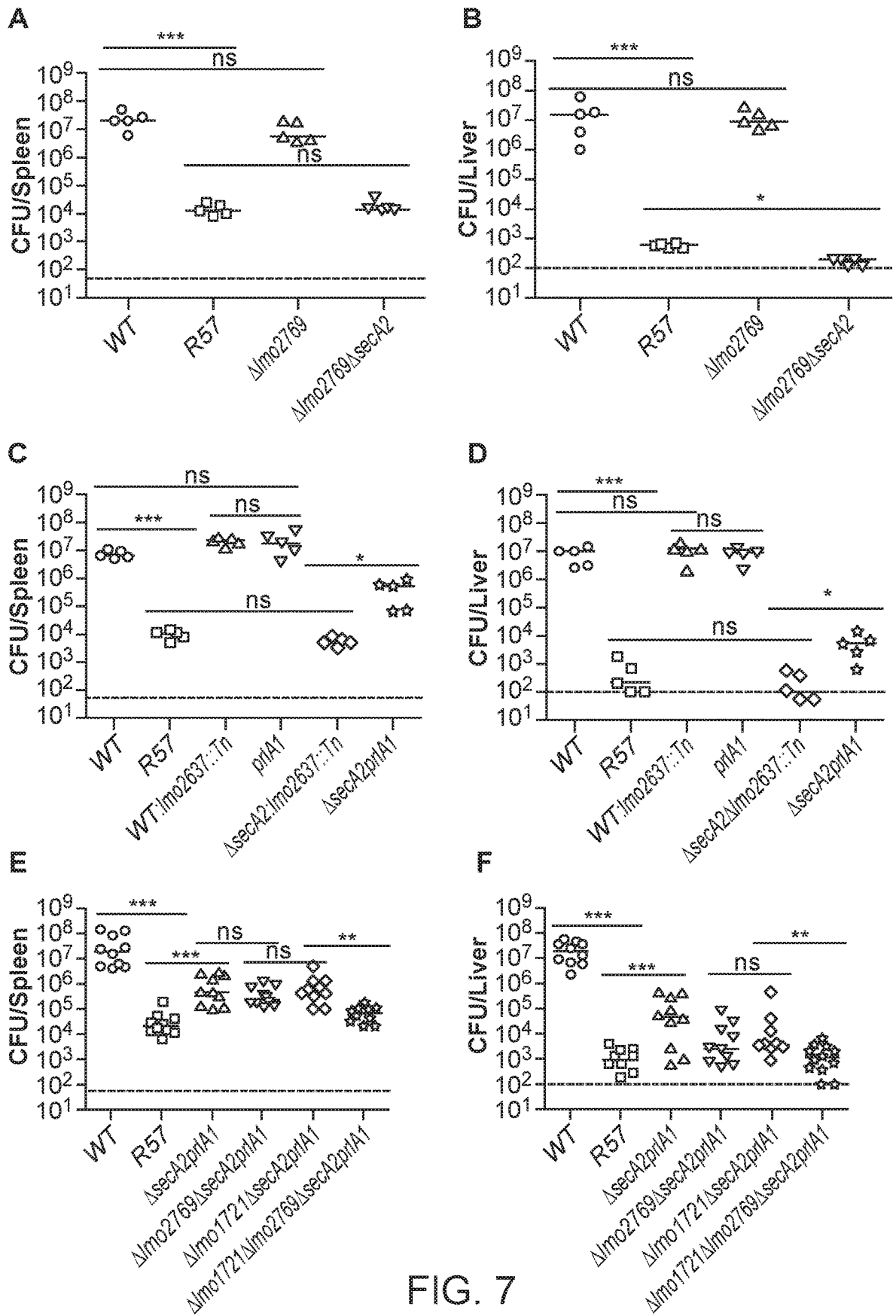
FIGS. 7A-7F: In vivo virulence of assorted mutants. Bacterial burdens in spleens and livers 48 hr post infection with $1 \times 10^5$ CFU in CD1 mice. The dashed-line represents the limit of detection. Statistical significance was evaluated using Mann Whitney test. ***P<0.0001, ns—P≥0.05.

Lysozyme susceptibility caused by the disruption of the lmo2769 operon had negligible impact on virulence (FIG. 4C and FIGS. 7A-B). Plaque size of the ΔsecA2Δlmo2769 double mutant increased 10% from that of ΔsecA2, however complementation of R57 with the lmo2769-lmo2767 operon had no effect on plaque formation of the revertant (FIG. 4C). We concluded that disruption of lmo2769 led to a cell wall defect that increased swarming motility of the mutant, but was not responsible for the increased plaque size in the originally isolated R57 suppressor strain.

Deletion of lmo1721, a gene harboring the second SNP identified in R57, had a suppressive effect on the swarming motility of ΔsecA2 and the double ΔsecA2Δlmo2769 mutants (FIG. 8D) and had no effect on lysozyme susceptibility (FIG. 6F). This gene encodes the transcriptional regulator LacR, which has been suggested to suppress virulence in *L. monocytogenes* in response to cellobiose (Milenbachs et al., "Deregulation of *Listeria monocytogenes* virulence gene expression by two distinct and semi-independent pathways," Micobiology (2004) 150:321-333; Stoll & Goebel, "The major PEP-phosphotransferase systems (PTSs) for glucose, mannose and cellobiose of *Listeria monocytogenes*, and their significance for extra- and intracellular growth," Micobiology (2010) 156:1069-1083) in addition to regulating the phosphotransferase system (Dalet et al., "Characterization of a unique σ54-dependent PTS operon of the lactose family in *Listeria monocytogenes*," Biochimie (2003) 85:633-638). Plaque formation was unaffected by in-frame deletion of Δlmo1721 alone or in combination with a secA2 deletion (FIG. 4D), but had a suppressive effect on the Δlmo1721Δlmo2769 double mutant, suggesting that the combination of the two mutations negatively influence virulence when SecA2 is undisturbed. Collectively these observations suggest that the SNP in lmo1721 did not contribute to the revertant phenotype.

D. The secY Mutation Significantly Improved Virulence and Swarming Motility of ΔsecA2.

The third SNP identified in the R57 revertant was in lmo2612, encoding SecY, which resulted in amino-acid substitution G408R. The G408 residue corresponded to V411 when aligned to the *E. coli* SecY and mapped to the last transmembrane segment of the protein. Mutations in this region of *E. coli* SecY, such as L407R and I408N, have been described as protein localization (prl) mutations (Osborne et al., "PrlA suppressor mutations cluster in regions corresponding to three distinct topological domains," EMBO J. (1993) 12:3391-3398; Smith et al., "Modeling the effects of prl mutations on the *Escherichia coli* SecY complex," J. Bacteriol. (2005) 187:6454-6465; Lycklama a Nijeholt et al., "Immobilization of the plug domain inside the SecY channel allows unrestricted protein translocation," J. Biol. Chem. (2010) 285:23747-23754.). We refer to the *L. monocytogenes* secY (G408R) allele as prlA1 in the remainder of this manuscript.

Figure 8:
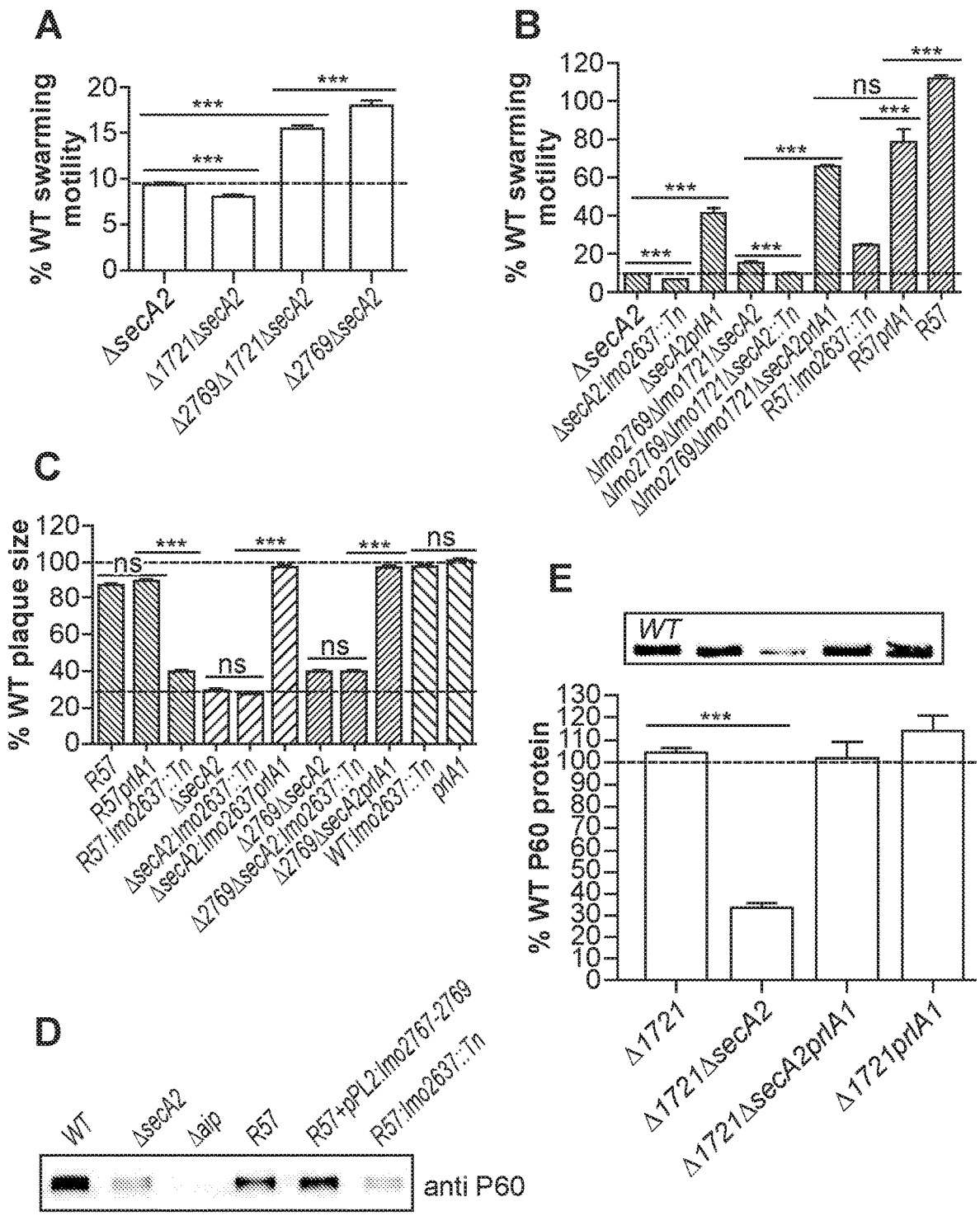
FIGS. 8A-8E: Swarming motility of lmo1721 FIG. 8A) and lmo2637::Tn FIG. 8B) mutants was assessed on semi-solid LB agar following incubation at 30° C. after 48 hr. Motility is expressed as a percentage of swarming area of the WT strain. Error bars represent standard deviations of the mean zone ratio between three independent experiments.

As in other bacteria, secY is essential in *L. monocytogenes* (Hossain et al., "Identification of putative drug targets of *Listeria monocytogenes* F2365 by subtractive genomics approach," J. Bio. Sci. Biotech. (2013) 2:63-71.) and is transcribed with other essential genes in a 28-gene operon. Attempts to introduce the prlA1 mutation into a WT background by allelic exchange at the native secY locus were unsuccessful. Therefore, we used phage transduction utilizing a Himar1 transposon insertion in a neighboring gene (lmo2637) as an antibiotic marker to transduce the prlA1 allele from the R57 revertant and the WT secY into various strains. Disruption of lmo2637 had a minor effect on swarming motility (FIG. 8A) but no effect on virulence (FIGS. 8C and 7C-D).

Introduction of the prlA1 mutation into the ΔsecA2 strain or the ΔsecA2Δlmo2769 double mutant resulted in enhanced motility (FIG. 5A) and restored the smooth colony morphology of these mutants. In addition, motility of R57 diminished significantly (88%) upon replacement of prlA1 with the WT allele (FIG. 5A), which was coupled with a change in colony morphology from smooth to rough. This suggested that the prlA1 mutation significantly contributed to the R57 motility and cell morphology phenotypes.

Figure 5:
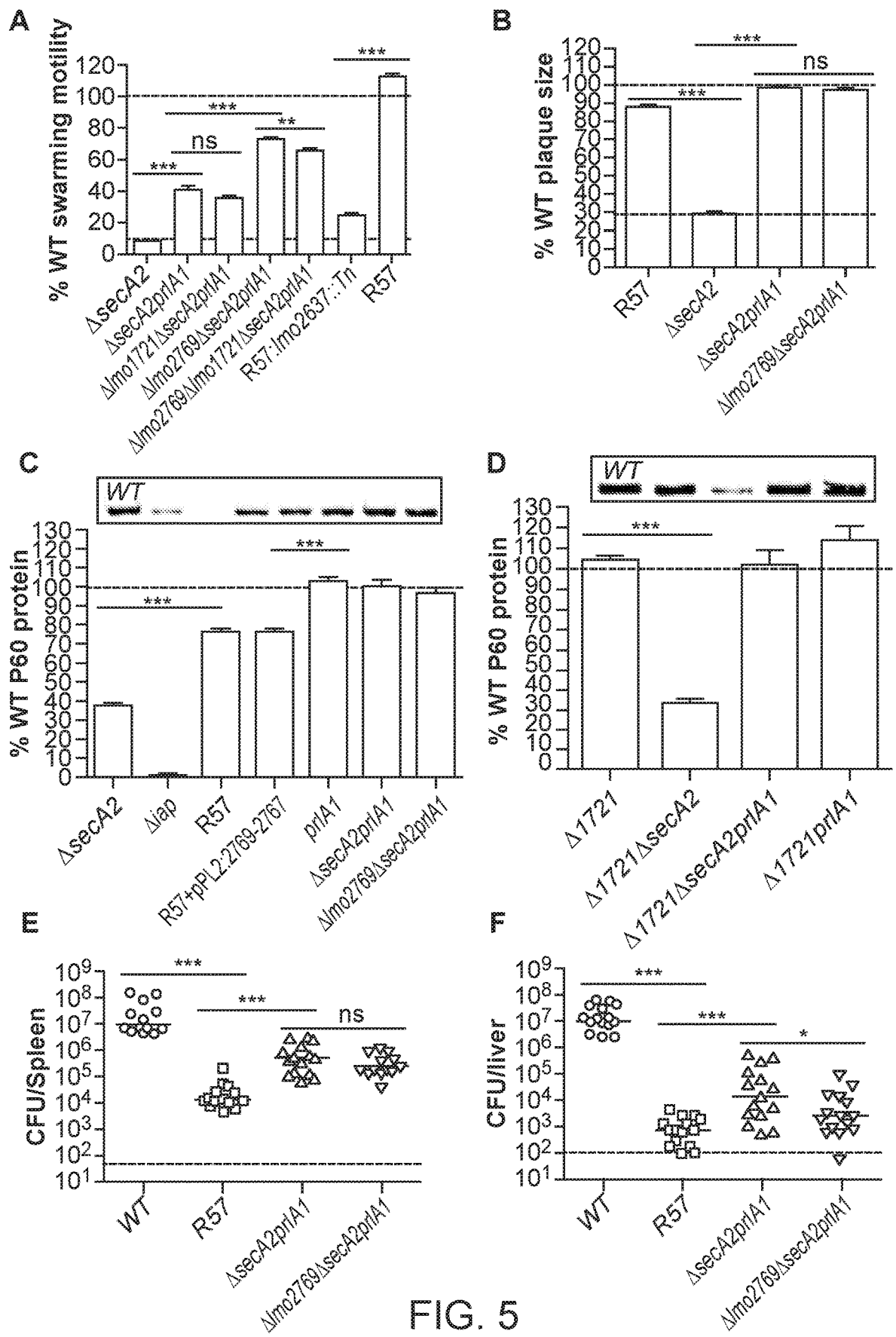
FIGS. 5A-5F: Characterization of the prlA1 mutation.

Surprisingly the prlA1 mutation alone was sufficient to completely restore cell-to-cell spread of the ΔsecA2 and the ΔImo2769ΔsecA2 double mutants (FIG. 5B). Exchanging the prlA1 mutation for the WT allele in R57 decreased plaque formation from 87% to 39%, the level observed for the ΔImo2769ΔsecA2 double mutant (FIG. 8C).

To investigate whether destabilization of the SecY channel in response to the prlA1 mutation was sufficient to restore protein secretion in ΔsecA2 mutants, the abundance of P60 in the supernatants of mutant cultures was evaluated as a proxy for other SecA2-dependent proteins. Notably, P60 levels were completely restored to WT levels in the secA2 constructs expressing the prlA1 mutation (FIG. 5C). Restoration of P60 was entirely PrlA1-dependent as exchanging the prlA1 for the WT allele in R57 background diminished the secreted P60 levels to those observed for the ΔsecA2 parent strain (FIG. 8B). Further, to address the possibility of differing secretion levels between the WT and ΔsecA2prlA1 strains, we undertook a timed experiment in which secretion levels of P60 were assessed. The introduction of the prlA1 mutation restored the levels of P60 secretion in the ΔsecA2 strain, while not affecting the secretion of SecA-dependent listeriolysin O (LLO) (FIG. 5D). Interestingly, P60 levels of R57 mutant were only 80% of the WT strain (FIG. 5C) and were not directly linked to ΔImo1721 (FIG. 5D) or ΔImo2769 (FIG. 5C). Collectively these observations show that a prlA1 mutation alone was sufficient to overcome the motility, cell morphology and cell-to-cell spread phenotypes associated with ΔsecA2, by restoring secretion of the autolysin P60 and likely other SecA2-depended proteins to WT levels.

Lastly, the effect of the prlA1 allele on virulence in vivo was assessed. Somewhat surprisingly, a prlA1 mutation alone in a WT background did not affect virulence (FIG. 7C). However, virulence of both secA2 and the ΔImo2769ΔsecA2 double mutant were partially restored (FIG. 5E-F and FIGS. 7E-F). Whereas the secA2 mutant and the R57 suppressor were 1,000-fold less virulent in the spleen and 10,000-fold less virulent in the liver (FIG. 3C-D and FIG. 5E-F), the prlA1 mutation partially rescued virulence by approximately, 100-fold in the spleen and 20-fold in the liver (FIGS. 5E-F). Notably though, it was still considerably less virulent than WT (20-fold in the spleen and 1000-fold in the liver).

III. Discussion

Much of what is known about the general secretory pathway (Sec) in bacteria originates from seminal genetic studies that led to the identification and characterization of the Sec components including the SecYEG channel and SecA ATPase (Beckwith J, "The Sec-dependent pathway," Res. Microbiol (2013) 164:497-504; Kusters & Driessen, "SecA, a remarkable nanomachine," Cell. Mol. Life Sci. (2011) 68:2053-2066; Tam et al., "Investigating the SecY plug movement at the SecYEG translocation channel," EMBO J. (2005) 24:3380-3388; Flower A M, "The SecY translocation complex: convergence of genetics and structure, Trends Micribiol. (2007) 15:203-210; Osborne & Silhavy, "PrlA suppressor mutations cluster in regions corresponding to three distinct topological domains," EMBO J. (1993) 12:3391-3398; Smith et al., "Modeling the effects of prl mutations on the *Escherichia coli* SecY complex," J. Bacteriol. (2005) 187:6454-6465; Duong & Wickner, "The PrlA and PrlG phenotypes are caused by a loosened association among the translocase SecYEG subunits," EMBO J. (1999) 18:3263-3270). While the secA is essential in all bacteria, a subset of Gram-positive bacteria harbor an additional, nonessential homologous gene called secA2 (Feltcher & Braunstein, "Emerging themes in SecA2-mediated protein export," Nature Rev. Microbiol. (2012) 10:779-789; Lenz et al., "SecA2-dependent secretion of autolytic enzymes promotes *Listeria monocytogenes* pathogenesis," Proc. Nat'l Acad. Sci USA (2003)100:12432-12437; Rigel & Braunstein, "A new twist on an old pathway—accessory secretion systems," Mol. Microbiol. (2008) 69:291-302.; Bensing et al., "Selective transport by SecA2: An expanding family of customized motor proteins," Biochim. Biophys. Acta (2014) 1843:1674-1686; Schneewind & Missiakas, "Protein secretion and surface display in Gram-positive bacteria," Phil. Trans. R Soc. B (2012) 367:1123-1139; Nguyen-Mau et al., "Secretion genes as determinants of *Bacillus anthracis* chain length," J. Bacteriol (2012) 194: 3841-3850). Both pathogenic and nonpathogenic species of *Listeria* encode SecA2 (Mishra et al., "Genetic organisation and molecular characterization of secA2 locus in *Listeria* species," Gene (2011) 489:76-85), which facilitates the secretion of two major autolysins contributing to septation, swarming motility, plaque formation in tissue culture cells and virulence in mice (Lenz et al., "SecA2-dependent secretion of autolytic enzymes promotes *Listeria monocytogenes* pathogenesis," Proc. Nat'lAcad. Sci USA (2003)100:12432-12437; Lenz & Portnoy, "Identification of a second *Listeria* secA gene associated with protein secretion and the rough phenotype," Mol. Microbiol. (2002) 45:1043-1056; Machata et al., "Simultaneous deficiency of both MurA and p60 proteins generates a rough phenotype in *Listeria monocytogenes*," J. Bacteriol. (2005) 187:8385-8394; Mishra et al., "Genetic organisation and molecular characterization of secA2 locus in *Listeria* species," Gene (2011) 489:76-85). It remains unclear, however, why certain bacteria encode secA2 while others do not, and why secA2 is dispensable for cell viability.

In this study, we took advantage of the swarming motility defect to isolate spontaneous mutants capable of swarming motility (FIG. 1). One mutant was phenotypically very similar to WT and was characterized in depth, with its phenotype being genetically traced directly to a single amino acid mutation in SecY. Similar mutations in *E. coli* secY, called prlA alleles are gain-of-function mutations that expand the repertoire of substrates that can be exported (Flower, id.; Osborne & Silhavy, id.; Smith et al., id.; van der Wolk et al., "PrlA4 prevents the rejection of signal sequence defective preproteins by stabilizing the SecA-SecY interaction during the initiation of translocation," EMBO J (1998) 17:3631-3639). Our findings indicate that the secY mutant identified in this study, here named prlA1, rescued the *L. monocytogenes* secA2 mutant by allowing for secretion of proteins that are normally SecA2-dependent. Recent work in *Mycobacterium smegmatis* reported that increased SecY levels suppressed the severe phenotypes of a secA2 mutant (Ligon et al., "Suppressor analysis reveals a role for SecY in the SecA2-dependent protein export pathway of Mycobacteria," J. Bacteriol. (2013) 195:4456-4465), suggesting that SecA2-dependent protein secretion occurs through interaction with the canonical SecY. Thus, in both *L. monocytogenes* and *M. smegmatis,* the canonical secY is very likely part of the translocation pore for SecA2 substrates unlike other pathogenic bacteria including *Bacillus anthracis* and some *Streptococcus* and *Staphylococcus* species, all of which have SecA2 and SecY2 (Feltcher & Braunstein, "Emerging themes in SecA2-mediated protein export," Nature Rev. Microbiol. (2012) 10:779-789; Bensing et al., "Selective transport by SecA2: An expanding family of customized motor proteins," Biochim. Biophys. Acta (2014) 1843:1674-1686; Schneewind & Missiakas, "Protein secretion and surface display in Gram-positive bacteria," Phil. Trans. R Soc. B (2012) 367:1123-1139; Nguyen-Mau S, "Secretion genes as determinants of *Bacillus anthracis* chain length," J. Bacteriol. (2012) 194:3841-3850.).

Wild-type *L. monocytogenes* is highly lysozyme resistant (Rae et al., "Mutations of the *Listeria monocytogenes* peptidoglycan N-deacetylase and O-acetylase result in enhanced lysozyme sensitivity, bacteriolysis, and hyperinduction of innate immune pathways," Infect. Immun. (2011) 79:3596-3606; Burke et al., "*Listeria monocytogenes* is resistant to lysozyme by the regulation, not acquisition, of cell wall modifying enzymes," J. Bacteriol. (2014) JB.02053-02014; Boneca et al., "A critical role for peptidoglycan N-deacetylation in *Listeria* evasion from the host innate immune system," Proc. Nat'l Acad. Sci. USA (2007) 104:997-1002). One curious finding reported in this study was that all 70 suppressors were lysozyme-sensitive and in four of the five sequenced suppressor mutants, lysozyme sensitivity was caused by mutations in an uncharacterized ABC transporter encoded by the lmo2769-lmo2767 operon. Lysozyme susceptibility of the fifth mutant was likely due to a mutation in wall, which was previously shown to be required for lysozyme resistance (Burke et al., id.). The first gene in the lmo2769-lmo2767 operon, encodes an ATP-binding protein similar to a poorly characterized *B. subtilis* protein (YtrB) whose expression has been observed following exposure to cell wall acting agents (Dyer et al., "A molecular mechanism of bacterial flagellar motor switching," J. Mol. Biol. (2009) 388:71-84). Mutation of either lmo2769 or lmo2768 conferred lysozyme susceptibility, suggesting that these mutations altered the cell wall and may have led to decreased chaining and increased swarming. Although the exact function of this operon requires further characterization, these data suggest that the lmo2769 operon is involved in maintaining cell wall homeostasis (Collins et al., "The ABC transporter AnrAB contributes to the innate resistance of *Listeria monocytogenes* to nisin, bacitracin, and various β-lactam antibiotics," Antimicrob. Agents Chemother. (2010) 54:4416-4423; Cuthbertson et al., "ABC transporters involved in export of cell surface glycoconjugates," Microbiol Mol. Biol. Rev. (2010) 74:341-362). The high frequency of mutations detected in this operon, associated with increased swarming, likely provided a growth advantage in semisolid media that increased the probability of acquiring less frequent mutations, for example the prlA1.

The prlA1 allele characterized in this study resulted in a glycine substitution for arginine (G408R) in the tenth transmembrane helix of SecY. Variations in this region of SecY in *E. coli,* such as L407R (PrlA301) and I408N (PrlA4), as well as PrlA-like mutation in the accessory SecY2 of *Streptococcus gordonii* (Bensing & Sullam, "Transport of preproteins by the accessory Sec system requires a specific domain adjacent to the signal peptide," J. Bacteriol (2010) 192:4223-4232), promote translocation of proteins with defective signal peptides by destabilizing the pore ring within the SecYEG channel (Osborne & Silhavy, id.; Smith et al., id.; Lycklama a Nijeholt et al., "Immobilization of the plug domain inside the SecY channel allows unrestricted protein translocation," J. Biol. Chem. (2010) 285:23747-23754). It is likely that the substitution of a hydrophobic glycine for a positively charged hydrophilic arginine residue would also induce a conformational change to the pore ring. The results indicate that the rescue in protein secretion is a result of a more efficient interaction between SecA and SecY induced by the conformational change of the pore ring, similar to that observed in a PrlA4 variant of *E. coli* (van der Wolk et al., id.; de Keyzer et al., "The F286Y mutation of PrlA4 tempers the signal sequence suppressor phenotype by reducing the SecA binding affinity," FEBS Lett. (2002) 510:17-21).

Protein secretion is an energetically costly process and in the absence of SecA2, another ATPase, such as SecA, is required to provide energy for translocation of P60 in the *L. monocytogenes* ΔsecA2prlA1 mutant. Since SecA is dimeric during protein translocation (Kusters et al., "Quaternary structure of SecA in solution and bound to SecYEG probed at the single molecule level," Structure (2011) 19:430-439) it is possible that SecA2 and SecA form a heterodimer, which interacts with the SecYEG, thereby modulating substrate specificity of the channel. The interaction between SecA2 and the canonical SecA ATPase has previously been shown to occur in *Streptococcus* (Zhou et al., "Canonical SecA associates with an accessory secretory protein complex involved in biogenesis of a Streptococcal serine-rich repeat gycoprotein," J. Bacteriol. (2011) 193:6560-6566) and implied in Mycobacteria (Rigel et al., "The accessory SecA2 system of Mycobacteria requires ATP binding and the canonical SecA1," J. Biol. Chem/(2009) 284:9927-9936) and more recently in *Listeria* (Halbedel et al., "A systematic proteomic analysis of *Listeria monocytogenes* house-keeping protein secretion systems," Mol. Cell Proteomics (2014) mcp.M114.041327). In the absence of a functional SecA2, SecA may drive SecA2-dependent secretion, although at a much lower rate, potentially due to a lower affinity of SecA alone for the specific substrates. This view is supported by the observation that the export of P60 and other SecA2-dependent proteins is not completely abolished in the secA2 mutant (Lenz et al., id.; Lenz & Portnoy, id.).

Although not yet characterized, we also identified a suppressor mutation in secA, providing further support for a possible interaction between SecA2 and SecA in *L. monocytogenes*. This mutation resulted in an amino-acid substitution D599N corresponding to D649 in the second nucleotide-binding domain of SecA in *E. coli*. Amino acid alterations in this region of SecA, in particular residues 631 to 653, are known as azi as these confer azide resistance resulting from an increased ATPase activity (Das et al., "The variable subdomain of *Escherichia coli* SecA functions to regulate SecA ATPase activity and ADP release," J. Bacteriol. (2012) 194:2205-2213; Schmidt et al., "Nucleotide binding activity of SecA homodimer is conformationally regulated by temperature and altered by prlD and azi mutations," J. Biol. Chem. (2000) 275:15440-15448) in addition to having an increased affinity for SecY (Schmidt et al., id.). A SecA homodimer with enhanced affinity for SecY either through prlA1 or azi mutations may suffice in overcoming the requirement for SecA2 in a secA2 mutant. The enhanced interaction of SecA with SecY would indirectly increase the rate of secretion of SecA2-dependent proteins independent of altering affinity of the ATPase for these substrates.

Another piece of evidence supporting the interaction between the two ATPases comes from a recent proteomics study, which showed that P60 secretion is indistinguishable between WT *L. monocytogenes* EGD-e and ΔsecA2 when grown in a defined medium at 37° C., but was diminished in the mutant at 20° C. (Renier et al., "Exoproteomic analysis of the SecA2-dependent secretion in *Listeria monocytogenes* EGD-e," J. Proteomics (2013) 80:183-195), thus suggesting that SecA2-dependent secretion is able to engage an alternative pathway under different environmental conditions. One ATPase or dimer combination may be favored over the other depending on the energetic state of the cell.

For example, the affinity of SecA2 for ATP in Mycobacteria is higher than that of SecA (Hou et al., "ATPase activity of *Mycobacterium tuberculosis* SecA1 and SecA2 proteins and its importance for SecA2 function in macrophages," J. Bacteriol. (2008) 190:4880-4887). In order not to compete for substrate, SecA2 is bound to ADP in a dormant state until it is required (D'Lima et al., "ADP-dependent conformational changes distinguish *Mycobacterium tuberculosis* SecA2 from SecA1," J. Biol. Chem. (2014) 289:2307-2317). Considering there is no conservation in the signal peptides of proteins being secreted through the SecA2-dependent pathway in *L. monocytogenes*, it remains unclear how proteins are targeted to the SecA2 (Lenz et al., id.; Renier et al., id.) and how that can be overcome in certain conditions.

It is curious why *Listeria* species require SecA2 for normal septation, while most other bacteria use other SecA2-independent mechanisms. One possibility is that secA2 mutants have an advantage under certain conditions. Indeed, secA2 mutants arise spontaneously in the lab as rough colonies that emanate from a smooth colony and spread on solid media (Lenz & Portnoy, id.; Monk et al., "Morphotypic conversion in *Listeria monocytogenes* biofilm formation: biological significance of rough colony isolates," Appl. Environ. Microbiol. (2004) 70:6686-6694; Gutekunst et al., "A filamentous-like mutant of *Listeria monocytogenes* with reduced expression of a 60-kilodalton extracellular protein invades and grows in 3T6 and Caco-2 cells," Can. J. Microbiol. (1992) 38:843-851). At ambient temperatures, these mutants readily form distinct filamentous biofilms, which are thicker than those formed by the WT strain (24, 69). The spontaneous and reversible morphologic conversion to a rough phenotype may provide a potential advantage to *L. monocytogenes* in its saprophytic phase by enhancing the ability to colonize abiotic surfaces. This may also be one of the reasons why the nonpathogenic *Listeria* species have retained SecA2, however, this potential advantage outside the host comes at a significant cost to its pathogenic phase, as *L. monocytogenes* secA2 mutants are approximately 1,000-fold attenuated for virulence in mice (FIG. 3C-D and (Lenz et al., id.; Lenz & Portnoy, id.; Machata et al., "Simultaneous deficiency of both MurA and p60 proteins generates a rough phenotype in *Listeria monocytogenes*," J. Bacteriol. (2005) 187:8385-8394), although rough mutants can persist in the gut (Zachar & Savage, "Microbial interference and colonization of the murine gastrointestinal tract by *Listeria monocytogenes*," Infect. Immun. (1979) 23:168-174) and the gallbladder (Hardy et al., "Extracellular replication of *Listeria monocytogenes* in the murine gall bladder," Science (2004) 303:851-853). Some of this attenuation has been traced to the lower levels of secreted autolysins primarily P60 and to a lesser extend NamA (Lenz et al., id.). However, even though the prlA1 mutation described in the study restored WT levels of secreted P60 and cell-to-cell spread, it only resulted in a 100-fold rescue in virulence in vivo of the attenuated secA2 mutant. The suppressor mutant was still less virulent than the WT strain suggesting that a functional SecA2 is still required for full expression of *L. monocytogenes* virulence. SecA2-dependent secretion may have evolved in *L. monocytogenes* to provide a mechanism for switching between the parasitic and the saprophytic phase thus providing an advantage in its ability to thrive in the environment as well as inside a host.

VI. Summary

The bulk of bacterial protein secretion occurs through the conserved SecY translocation channel that is powered by SecA-dependent ATP hydrolysis. Many Gram-positive bacteria, including the human pathogen Listeria monocytogenes, possess an additional nonessential specialized ATPase, SecA2. SecA2-dependent secretion is required for normal cell morphology and virulence in *L. monocytogenes*; however, the mechanism of export via this pathway is poorly understood. *L. monocytogenes* secA2 mutants form rough colonies, have septation defects, are impaired for swarming motility, and form small plaques in tissue culture cells. In this study, 70 spontaneous mutants were isolated that restored swarming motility to *L. monocytogenes* secA2 mutants. Most of the mutants had smooth colony morphology and septated normally, but all were lysozyme sensitive. Five representative mutants were subjected to whole-genome sequencing. Four of the five had mutations in proteins encoded by the lmo2769 operon that conferred lysozyme sensitivity and increased swarming but did not rescue virulence defects. A point mutation in secY was identified that conferred smooth colony morphology to secA2 mutants, restored wild-type plaque formation, and increased virulence in mice. This secY mutation resembled a prl suppressor known to expand the repertoire of proteins secreted through the SecY translocation complex. Accordingly, the ΔsecA2prlA1 mutant showed wild-type secretion levels of P60, an established SecA2-dependent secreted autolysin. Although the prl mutation largely suppressed almost all of the measurable SecA2-dependent traits, the ΔsecA2prlA1 mutant was still less virulent in vivo than the wild-type strain, suggesting that SecA2 function was still required for pathogenesis.

Notwithstanding the appended clauses, the disclosure set forth herein is also defined by the following clauses:

1. A *Listeria* bacterium comprising a general secretory pathway (GSP) mutation and a heterologous nucleic acid.

2. The *Listeria* bacterium according to Clause 1, wherein the GSP mutation results in enhanced protein secretion.

3. The *Listeria* bacterium according to Clauses 1 or 2, wherein the GSP pathway mutation comprises a mutant GSP protein.

4. The *Listeria* bacterium according to Clause 3, wherein the mutant GSP protein is a mutant of SecY or SecA.

5. The *Listeria* bacterium according to Clause 4, wherein the mutant GSP protein is a SecY mutant.

6. The *Listeria* bacterium according to Clause 5, where the SecY mutant results in a conformational change of a translocation pore configuration.

7. The *Listeria* bacterium according to Clauses 4 or 5, wherein the SecY mutant comprises a protein localization (PRL) mutation.

8. The *Listeria* bacterium according to any of Clauses 5 to 7, wherein the Sec Y mutant comprises a mutation in the SecY tenth transmembrane helix.

9. The *Listeria* bacterium according to Clause 8, wherein the mutation comprises a substitution mutation.

10. The *Listeria* bacterium according to Clause 9, wherein the mutation comprises a substitution of a hydrophobic residue for a hydrophilic residue.

11. The *Listeria* bacterium according to Clause 10, wherein the mutation comprises a mutation at G408.

12. The *Listeria* bacterium according to Clause 11, wherein the mutation comprises a G408R mutation.

13. The *Listeria* bacterium according to Clause 4, wherein the mutant GSP protein is a SecA mutant.

14. The *Listeria* bacterium according to Clause 13, wherein the SecA mutant comprises an AZI mutation.

15. The *Listeria* bacterium according to Clauses 13 or 14, wherein the SecA mutant comprises a substitution mutation.

16. The *Listeria* bacterium according to Clause 13, wherein the substitution mutation comprises a conserved mutation.

17. The *Listeria* bacterium according to Clause 16, wherein the conserved mutation comprises a substitution of polar residues.

18. The *Listeria* bacterium according to Clause 17, wherein the mutation comprises a mutation at D599.

19. The *Listeria* bacterium according to Clause 18, wherein the mutation comprises a D599N mutation.

20. The *Listeria* bacterium according to any of the preceding clauses, wherein the heterologous nucleic acid is integrated.

21. The *Listeria* bacterium according to Clause 20, wherein the heterologous nucleic acid encodes at least one product.

22. The *Listeria* bacterium according to Clause 21, wherein the at least one product is an antigen.

23. The *Listeria* bacterium according to Clause 22, wherein the antigen is secreted by a SecA2 mediated pathway.

24. The *Listeria* bacterium according to any of the preceding clauses, wherein the bacterium is attenuated.

25. The *Listeria* bacterium according to any of the preceding clauses, wherein the bacterium comprises a SecA2 mutant.

26. The *Listeria* bacterium according to any of the preceding clauses, wherein the *Listeria* bacterium is *Listeria monocytogenes*.

27. A vaccine comprising a *Listeria* bacterium according to any of Clauses 1 to 26.

28. A method of eliciting or boosting a cellular immune response in a subject, said method comprising:
administering to said subject an effective amount of a vaccine according to Clause 27.

29. A method of delivering a nucleic acid or polypeptide into a cell, said method comprising:
introducing into said cell a *Listeria* bacterium according to any of Clauses 1 to 26, wherein said *Listeria* bacterium comprises nucleotide coding sequence for the nucleic acid or protein.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A *Listeria* bacterium comprising:
   an expressed mutant SecY mutant protein comprising a mutation at G408 that enhances protein secretion as compared to a control; and
   a heterologous nucleic acid.

2. The *Listeria* bacterium according to claim 1, wherein the mutation comprises a substitution mutation.

3. The *Listeria* bacterium according to claim 1, wherein the heterologous nucleic acid is integrated.

4. The *Listeria* bacterium according to claim 1, wherein the *Listeria* bacterium is *Listeria monocytogenes*.

5. A vaccine comprising a *Listeria* bacterium according to claim 1.

6. A method of eliciting or boosting a cellular immune response in a subject, said method comprising:
   administering to said subject an effective amount of a vaccine according to claim 5.

7. A method of delivering a nucleic acid or polypeptide into a cell, said method comprising:
   introducing into said cell a *Listeria* bacterium according to claim 1, wherein said *Listeria* bacterium comprises a nucleotide coding sequence for the nucleic acid or protein.

8. The *Listeria* bacterium according to claim 1, wherein the enhanced protein secretion comprises increased p60 secretion as compared to a control.

9. The *Listeria* bacterium according to claim 1, wherein the enhanced protein secretion comprises increased secretion of a protein encoded by the heterologous nucleic acid as compared to a control.

10. The *Listeria* bacterium according to claim 1, wherein the enhanced protein secretion comprises an increase in the diversity of proteins that are secreted by the *Listeria* as compared to a control.

11. The *Listeria* bacterium according to claim 1, further comprising one or more further mutations that confers an attenuated phenotype.

* * * * *

SEQUENCE LISTING

```
<160> NUMBER OF SEQ ID NOS: 10

<210> SEQ ID NO 1
<211> LENGTH: 32
<212> TYPE: DNA
<213> ORGANISM: Artificial sequence
<220> FEATURE:
<223> OTHER INFORMATION: synthetic oligonucleotide sequence

<400> SEQUENCE: 1
attagtcgac ctcggagttt ggtgtcttct gg                              32

<210> SEQ ID NO 2
<211> LENGTH: 30
<212> TYPE: DNA
<213> ORGANISM: Artificial sequence
<220> FEATURE:
<223> OTHER INFORMATION: synthetic oligonucleotide sequence

<400> SEQUENCE: 2
attactgcag aaacgatgcg gactcaaacg                                 30

<210> SEQ ID NO 3
<211> LENGTH: 48
<212> TYPE: DNA
<213> ORGANISM: Artificial sequence
```

```
<220> FEATURE:
<223> OTHER INFORMATION: synthetic oligonucleotide sequence

<400> SEQUENCE: 3
ctcccgtctg ttttaaatct cgtatttagt taagttccga attttcat            48

<210> SEQ ID NO 4
<211> LENGTH: 48
<212> TYPE: DNA
<213> ORGANISM: Artificial sequence
<220> FEATURE:
<223> OTHER INFORMATION: synthetic oligonucleotide sequence

<400> SEQUENCE: 4
atgaaaattc ggaacttaac taaatacgag atttaaaaca gacgggag             48

<210> SEQ ID NO 5
<211> LENGTH: 30
<212> TYPE: DNA
<213> ORGANISM: Artificial sequence
<220> FEATURE:
<223> OTHER INFORMATION: synthetic oligonucleotide sequence

<400> SEQUENCE: 5
attagtcgac acagatgtag cggctcgtgg                                 30

<210> SEQ ID NO 6
<211> LENGTH: 48
<212> TYPE: DNA
<213> ORGANISM: Artificial sequence
<220> FEATURE:
<223> OTHER INFORMATION: synthetic oligonucleotide sequence

<400> SEQUENCE: 6
gattcctttt tcttaatttt cttcgacttc ttcttttcta ctagacat             48

<210> SEQ ID NO 7
<211> LENGTH: 48
<212> TYPE: DNA
<213> ORGANISM: Artificial sequence
<220> FEATURE:
<223> OTHER INFORMATION: synthetic oligonucleotide sequence

<400> SEQUENCE: 7
atgtctagta gaaaagaaga agtcgaagaa aattaagaaa aaggaatc             48

<210> SEQ ID NO 8
<211> LENGTH: 30
<212> TYPE: DNA
<213> ORGANISM: Artificial sequence
<220> FEATURE:
<223> OTHER INFORMATION: synthetic oligonucleotide sequence

<400> SEQUENCE: 8
attactgcag cgccgtccat tgttccatag                                 30

<210> SEQ ID NO 9
<211> LENGTH: 28
<212> TYPE: DNA
<213> ORGANISM: Artificial sequence
<220> FEATURE:
<223> OTHER INFORMATION: synthetic oligonucleotide sequence

<400> SEQUENCE: 9
attagtcgac ctggatgtgg cgtaaggg                                   28
```

```
<210> SEQ ID NO 10
<211> LENGTH: 32
<212> TYPE: DNA
<213> ORGANISM: Artificial sequence
<220> FEATURE:
<223> OTHER INFORMATION: synthetic oligonucleotide sequence

<400> SEQUENCE: 10
attaggatcc cataactttg tcccgattgt cc                                    32
```